United States Patent
Cetti et al.

(10) Patent No.: US 10,716,743 B2
(45) Date of Patent: *Jul. 21, 2020

(54) PERSONAL CARE COMPOSITIONS AND METHODS

(71) Applicant: The Procter & Gamble Company, Cincinnati, OH (US)

(72) Inventors: Jonathan Robert Cetti, Mason, OH (US); Jiten Odhavji Dihora, Liberty Township, OH (US); Steven Edward Witt, Morrow, OH (US); Eric Shane Henley, West Harrison, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/531,761

(22) Filed: Aug. 5, 2019

(65) Prior Publication Data

US 2020/0009032 A1   Jan. 9, 2020

Related U.S. Application Data

(60) Continuation of application No. 16/189,360, filed on Nov. 13, 2018, now Pat. No. 10,413,493, which is a
(Continued)

(51) Int. Cl.
*A61K 8/28* (2006.01)
*A61K 8/11* (2006.01)
(Continued)

(52) U.S. Cl.
CPC .............. *A61K 8/28* (2013.01); *A61K 8/0229* (2013.01); *A61K 8/11* (2013.01); *A61K 8/25* (2013.01);
(Continued)

(58) Field of Classification Search
CPC . A61K 8/28; A61K 8/25; A61K 8/583; A61K 8/732; A61K 8/922; A61K 8/0229; A61Q 15/00
See application file for complete search history.

(56) References Cited

U.S. PATENT DOCUMENTS

| 5,254,332 A | 10/1993 | Greczyn et al. |
| 5,302,381 A | 4/1994 | Greczyn et al. |

(Continued)

FOREIGN PATENT DOCUMENTS

| DE | 19821691 A1 | 11/1999 |
| DE | 19944545 C1 | 3/2001 |

(Continued)

OTHER PUBLICATIONS

Aston Chemicals, Performathox 450 (http://www.aston-chemicals.com/single-product?id-620), © 2015, p. 1.
(Continued)

*Primary Examiner* — Carlos A Azpuru
(74) *Attorney, Agent, or Firm* — Kathleen Y. Carter

(57) ABSTRACT

Methods of making personal care compositions including microcapsules and methods of enhancing the efficacy of the microcapsules in said personal care compositions.

20 Claims, 1 Drawing Sheet

Related U.S. Application Data continuation of application No. 15/640,675, filed on Jul. 3, 2017, now Pat. No. 10,154,949, which is a continuation of application No. 15/412,341, filed on Jan. 23, 2017, now Pat. No. 9,750,671, which is a division of application No. 14/755,507, filed on Jun. 30, 2015, now Pat. No. 9,687,425.

(60) Provisional application No. 62/019,279, filed on Jun. 30, 2014.

(51) Int. Cl.

| | | |
|---|---|---|
| *A61Q 15/00* | (2006.01) | |
| *A61K 8/02* | (2006.01) | |
| *A61K 8/34* | (2006.01) | |
| *A61K 8/81* | (2006.01) | |
| *A61K 8/65* | (2006.01) | |
| *A61K 8/73* | (2006.01) | |
| *A61K 8/58* | (2006.01) | |
| *B01J 13/12* | (2006.01) | |
| *A61K 8/26* | (2006.01) | |
| *A61K 8/25* | (2006.01) | |
| *A61K 8/31* | (2006.01) | |
| *A61K 8/33* | (2006.01) | |
| *A61K 8/37* | (2006.01) | |
| *A61K 8/42* | (2006.01) | |
| *A61K 8/49* | (2006.01) | |
| *A61K 8/60* | (2006.01) | |
| *A61K 8/891* | (2006.01) | |
| *A61K 8/92* | (2006.01) | |

(52) U.S. Cl.
CPC ............... *A61K 8/26* (2013.01); *A61K 8/31* (2013.01); *A61K 8/33* (2013.01); *A61K 8/342* (2013.01); *A61K 8/37* (2013.01); *A61K 8/42* (2013.01); *A61K 8/498* (2013.01); *A61K 8/585* (2013.01); *A61K 8/60* (2013.01); *A61K 8/65* (2013.01); *A61K 8/732* (2013.01); *A61K 8/738* (2013.01); *A61K 8/8147* (2013.01); *A61K 8/8152* (2013.01); *A61K 8/891* (2013.01); *A61K 8/92* (2013.01); *A61K 8/922* (2013.01); *A61Q 15/00* (2013.01); *B01J 13/125* (2013.01); *A61K 2800/31* (2013.01); *A61K 2800/412* (2013.01); *A61K 2800/56* (2013.01); *A61K 2800/592* (2013.01); *A61K 2800/652* (2013.01); *A61K 2800/654* (2013.01); *A61K 2800/805* (2013.01)

(56) References Cited

U.S. PATENT DOCUMENTS

| | | | |
|---|---|---|---|
| 5,324,490 A | 6/1994 | Van | |
| 5,354,553 A | 10/1994 | Greczyn et al. | |
| 5,376,362 A | 12/1994 | Murphy et al. | |
| 5,378,452 A | 1/1995 | Greczyn | |
| 5,389,279 A | 2/1995 | Au et al. | |
| 5,417,964 A | 5/1995 | Carlson et al. | |
| 5,419,879 A | 5/1995 | Vlahakis et al. | |
| 5,435,590 A | 7/1995 | Van Vlahakis et al. | |
| 5,443,822 A | 8/1995 | Grec | |
| 5,487,887 A | 1/1996 | Benfatto | |
| 5,501,812 A | 3/1996 | Varmeer et al. | |
| 5,534,246 A | 7/1996 | Herb et al. | |
| 5,575,990 A | 11/1996 | Benfatto | |
| 5,603,925 A | 2/1997 | Ross et al. | |
| 5,650,140 A | 7/1997 | Bergmann et al. | |
| 5,650,141 A | 7/1997 | Bergmann et al. | |
| 5,650,142 A | 7/1997 | Bergmann et al. | |
| 5,650,143 A | 7/1997 | Bergmann | |
| 5,733,534 A | 5/1998 | Sawin et al. | |
| 5,750,096 A | 5/1998 | Guskey | |
| 5,840,286 A | 11/1998 | Gardlik et al. | |
| 5,840,287 A | 11/1998 | Guskey et al. | |
| 5,840,288 A | 11/1998 | Guskey et al. | |
| 5,846,520 A | 12/1998 | Guskey et al. | |
| 5,849,276 A | 12/1998 | Guskey et al. | |
| 5,861,145 A | 1/1999 | Lucas et al. | |
| 5,863,524 A | 1/1999 | Mason et al. | |
| 5,928,631 A | 7/1999 | Lucas et al. | |
| 5,972,319 A | 10/1999 | Linn et al. | |
| 5,997,850 A | 12/1999 | Tang et al. | |
| 6,071,975 A | 6/2000 | Halloran | |
| 6,110,451 A | 6/2000 | Matz et al. | |
| 6,171,601 B1 | 1/2001 | Gardlik et al. | |
| 6,187,300 B1 | 2/2001 | Motley et al. | |
| 6,277,359 B1 | 8/2001 | Raths et al. | |
| 6,383,503 B1 | 5/2002 | Blackmann et al. | |
| 6,387,357 B1 | 5/2002 | Chopra et al. | |
| 6,436,062 B1 | 8/2002 | Iwamoto et al. | |
| 6,436,382 B1 | 8/2002 | Chopra et al. | |
| 6,464,991 B1 | 10/2002 | Walele et al. | |
| 6,485,716 B1 | 11/2002 | Fei et al. | |
| 6,500,412 B1 | 12/2002 | Johansson et al. | |
| 6,503,491 B2 | 1/2003 | Guenin et al. | |
| 6,511,658 B2 | 1/2003 | Mattai et al. | |
| 6,534,045 B2 | 3/2003 | Mattai et al. | |
| 6,605,288 B1 | 8/2003 | Okawa et al. | |
| 6,608,126 B2 | 8/2003 | Ferritto et al. | |
| 6,649,577 B1 | 11/2003 | Bleckmann et al. | |
| 6,652,842 B2 | 11/2003 | Lucia et al. | |
| 6,652,867 B1 | 11/2003 | Vincent et al. | |
| 6,653,378 B2 | 11/2003 | Ferritto et al. | |
| 6,703,536 B2 | 3/2004 | Roe et al. | |
| 6,716,441 B1 | 4/2004 | Osborne et al. | |
| 6,774,179 B2 | 8/2004 | Ferritto et al. | |
| 6,787,603 B2 | 9/2004 | Johnson et al. | |
| 6,790,435 B1 | 9/2004 | Ma et al. | |
| 6,793,929 B2 | 9/2004 | Bleckmann et al. | |
| 6,803,399 B2 | 10/2004 | Ferritto et al. | |
| 6,821,934 B1 | 11/2004 | Bleckmann et al. | |
| 6,835,373 B2 | 12/2004 | Kolodzik et al. | |
| 6,835,374 B2 | 12/2004 | Parekh et al. | |
| 6,849,251 B2 | 2/2005 | Banowski et al. | |
| 6,916,465 B2 | 7/2005 | Panzer et al. | |
| 6,936,242 B2 | 8/2005 | Elliot et al. | |
| 6,942,871 B2 | 9/2005 | Bruning et al. | |
| 6,998,424 B2 | 2/2006 | Feng et al. | |
| 7,204,976 B2 | 4/2007 | Popoff et al. | |
| 7,235,251 B2 | 6/2007 | Hamer et al. | |
| 7,452,526 B2 | 11/2008 | Walling et al. | |
| 7,799,332 B2 | 9/2010 | Moghe et al. | |
| 7,867,506 B2 | 1/2011 | Moghe et al. | |
| 7,905,673 B2 | 3/2011 | Swaile et al. | |
| 8,187,578 B2 | 5/2012 | Walling et al. | |
| 8,343,467 B2 | 1/2013 | Woehrmann et al. | |
| 8,435,955 B2 | 5/2013 | Masiu et al. | |
| 8,461,258 B2 | 6/2013 | Iimura et al. | |
| 8,524,650 B2 | 9/2013 | Denutte et al. | |
| 8,546,483 B2 | 10/2013 | Tanaka et al. | |
| 8,849,251 B2 | 9/2014 | Khoury et al. | |
| 9,487,733 B2 | 11/2016 | Budijono et al. | |
| 9,687,425 B2 | 6/2017 | Cetti et al. | |
| 9,750,671 B2 * | 9/2017 | Cetti | A61K 8/26 |
| 10,154,949 B2 * | 12/2018 | Cetti | A61K 8/26 |
| 10,413,493 B2 * | 9/2019 | Cetti | A61K 8/11 |
| 2001/0012860 A1 | 8/2001 | Bleckmann et al. | |
| 2002/0122781 A1 | 9/2002 | Pinzon et al. | |
| 2003/0040571 A1 | 2/2003 | Feng et al. | |
| 2003/0082126 A9 | 5/2003 | Pinzon et al. | |
| 2003/0103921 A1 | 6/2003 | Brucks et al. | |
| 2003/0113282 A1 | 6/2003 | Buranachokpaisan | |
| 2003/0198653 A1 | 10/2003 | Walele et al. | |
| 2004/0166083 A1 | 8/2004 | Abrutyn | |
| 2004/0176464 A1 | 9/2004 | Kanatani et al. | |
| 2005/0095210 A1 | 5/2005 | Mattai et al. | |
| 2005/0118125 A1 | 6/2005 | Mattai et al. | |
| 2005/0191254 A1 | 9/2005 | Walling et al. | |
| 2005/0191257 A1 | 9/2005 | Brahms et al. | |

(56) References Cited

U.S. PATENT DOCUMENTS

| | | |
|---|---|---|
| 2005/0227906 A1 | 10/2005 | Schudel et al. |
| 2005/0288205 A1 | 12/2005 | Walele et al. |
| 2006/0013792 A1 | 1/2006 | Fontaine et al. |
| 2006/0073110 A1 | 4/2006 | Modi |
| 2006/0210502 A1 | 9/2006 | Galante et al. |
| 2006/0280716 A1 | 12/2006 | Czech et al. |
| 2007/0003499 A1 | 1/2007 | Shen et al. |
| 2007/0009472 A1 | 1/2007 | Niebauer et al. |
| 2007/0092541 A1 | 4/2007 | Walling |
| 2007/0166254 A1 | 7/2007 | Bianchi |
| 2009/0010972 A1 | 1/2009 | Modafari et al. |
| 2009/0016977 A1 | 1/2009 | Modafari et al. |
| 2009/0087396 A1 | 4/2009 | Hwang et al. |
| 2009/0123392 A1 | 5/2009 | Braun et al. |
| 2009/0253612 A1 | 10/2009 | Mushrock et al. |
| 2009/0298936 A1 | 12/2009 | Clothier et al. |
| 2009/0304617 A1 | 12/2009 | Banowski |
| 2010/0112017 A1 | 5/2010 | Mizutani et al. |
| 2010/0196515 A1 | 8/2010 | Kamiya et al. |
| 2012/0045493 A1 | 2/2012 | Popoff et al. |
| 2012/0135056 A1 | 5/2012 | Yarlagadda et al. |
| 2012/0205002 A1 | 8/2012 | Walling et al. |
| 2012/0282309 A1 | 11/2012 | Dihora |
| 2012/0321578 A1 | 12/2012 | Leuridan et al. |
| 2013/0052144 A1 | 2/2013 | Claas et al. |
| 2013/0189204 A1 | 7/2013 | Duggal et al. |
| 2013/0280409 A1 | 10/2013 | Mushrock et al. |
| 2013/0302392 A1 | 11/2013 | Mistry et al. |
| 2013/0316937 A1 | 11/2013 | Denutte et al. |
| 2014/0079748 A1 | 3/2014 | Cetti |
| 2014/0260103 A1 | 9/2014 | Sturgis et al. |
| 2014/0271514 A1 | 9/2014 | Sturgis et al. |
| 2014/0271515 A1 | 9/2014 | Sturgis et al. |
| 2014/0271516 A1 | 9/2014 | Sturgis et al. |
| 2015/0374593 A1 | 12/2015 | Cetti et al. |
| 2015/0374609 A1 | 12/2015 | Cetti et al. |
| 2017/0128333 A1 | 5/2017 | Cetti |
| 2017/0296449 A1 | 10/2017 | Cetti |
| 2019/0083374 A1 | 3/2019 | Cetti |

FOREIGN PATENT DOCUMENTS

| | | |
|---|---|---|
| DE | 10057767 A1 | 5/2002 |
| EP | 0 922 449 A2 | 6/1999 |
| EP | 0 965 331 A3 | 12/1999 |
| EP | 0965331 A2 | 12/1999 |
| EP | 1 158 956 A1 | 12/2001 |
| EP | 1 183 003 B1 | 3/2002 |
| EP | 1 195 154 A2 | 4/2002 |
| EP | 2 314 270 A2 | 4/2011 |
| EP | 1 776 081 B1 | 8/2011 |
| FR | 2926219 A1 | 7/2009 |
| FR | 2954094 A1 | 6/2011 |
| GB | 2299270 A | 10/1996 |
| JP | 05115538 A | 5/1993 |
| JP | 06007415 A | 1/1994 |
| JP | 06262060 A | 9/1994 |
| JP | 08010314 A | 1/1996 |
| JP | 09157147 A | 6/1997 |
| JP | 10094591 A | 4/1998 |
| JP | 10147793 A | 6/1998 |
| JP | 10183172 A | 7/1998 |
| JP | 11106315 A | 4/1999 |
| JP | 11106330 A | 4/1999 |
| JP | 11106781 A | 4/1999 |
| JP | 2002 114633 A | 4/2000 |
| JP | 2000 186025 A | 7/2000 |
| JP | 2000 186026 A | 7/2000 |
| JP | 2000 229826 A | 8/2000 |
| JP | 2000 300652 A | 10/2000 |
| JP | 2003 335629 A | 11/2000 |
| JP | 2000 133968 A | 12/2001 |
| JP | 2001333968 A | 12/2001 |
| JP | 2003 081763 A | 3/2003 |
| JP | 2003 300813 A | 10/2003 |
| JP | 2004 049889 A | 2/2004 |
| JP | 2004 137227 A | 5/2004 |
| JP | 2004 337367 A | 12/2004 |
| JP | 2005 082484 A | 3/2005 |
| JP | 2005 145877 A | 6/2005 |
| JP | 2006 036981 A | 2/2006 |
| JP | 2006 087903 A | 4/2006 |
| JP | 2007 044422 A | 2/2007 |
| JP | 2008 093207 A | 4/2008 |
| JP | 2008 289783 A | 12/2008 |
| JP | 2009 001508 A | 1/2009 |
| JP | 2009 120525 A | 6/2009 |
| JP | 2009 161474 A | 7/2009 |
| JP | 2010 141880 A | 6/2010 |
| JP | 2011 148785 A | 8/2011 |
| KR | 2009 0107340 A | 10/2009 |
| KR | 2009 0129849 A | 12/2009 |
| WO | WO 1994/09754 A1 | 5/1994 |
| WO | WO 1996/24326 A1 | 8/1996 |
| WO | WO 1996/37184 A1 | 11/1996 |
| WO | WO 1998/55088 A1 | 12/1998 |
| WO | WO 2000/67713 A1 | 11/2000 |
| WO | WO 2001/13871 A1 | 3/2001 |
| WO | WO 2001/15659 A2 | 3/2001 |
| WO | WO 2003/53388 A1 | 7/2003 |
| WO | WO 2003/02610 A1 | 9/2003 |
| WO | WO2003072610 A1 | 9/2003 |
| WO | WO 2004/050045 A1 | 6/2004 |
| WO | WO 2005/099661 A1 | 10/2005 |
| WO | WO 2007/099738 A1 | 9/2007 |
| WO | WO2007/114329 A1 | 10/2007 |
| WO | WO2009/138150 A1 | 11/2009 |

OTHER PUBLICATIONS

Flick, Cosmetic Additives, 1991, Noyes Publications, p. 18.

Laden, Antiperspirant and Deodorants, Second Edition, 1999, pp. 140-141.

PCT International Search Report and Written Opinion of the International Searching Authority dated Oct. 13, 2014, PCT/US2014/024337, 13 pages.

PCT International Search Report and Written Opinion of the International Searching Authority dated Oct. 9, 2014, PCT/US2014/024148, 14 pages.

PCT International Search Report and Written Opinion of the International Searching Authority dated Oct. 9, 2014, PCT/US2014/024166, 13 pages.

PCT International Search Report and Written Opinion of the International Searching Authority dated Sep. 15, 2015, PCT/US2015/038403, 9 pages.

PCT International Search Report and Written Opinion of the International Searching Authority dated Sep. 9, 2015, PCT/US2015/038402, 11 pages.

\* cited by examiner

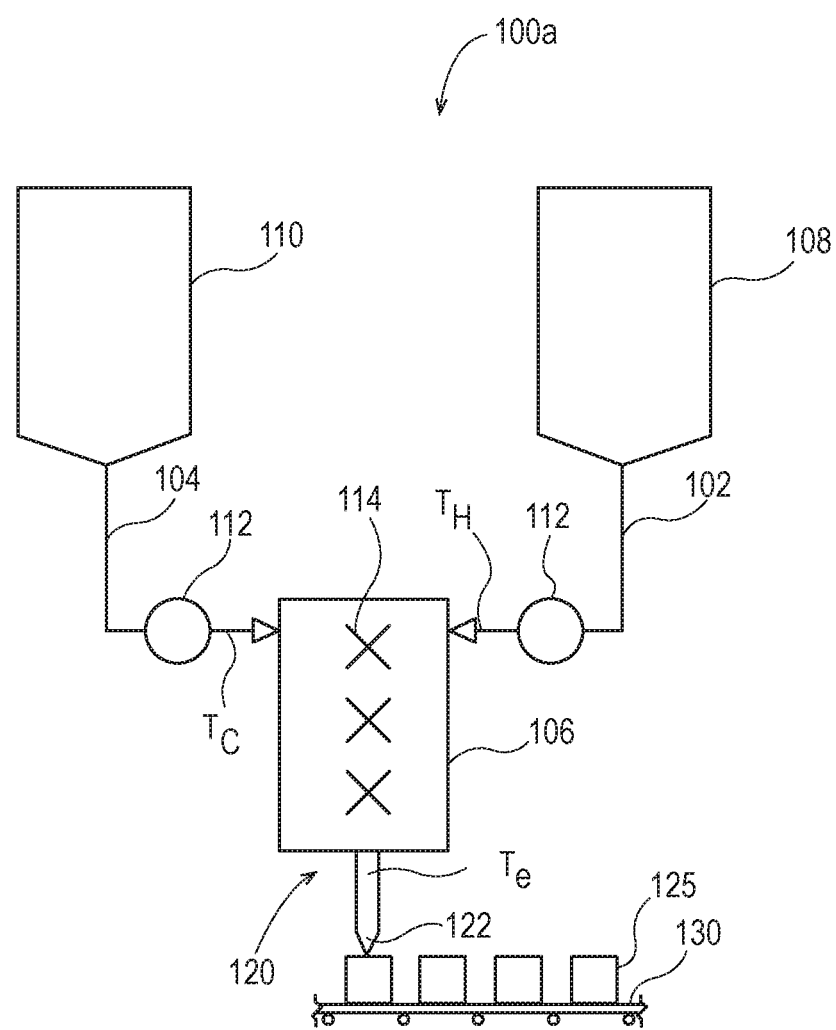

PERSONAL CARE COMPOSITIONS AND METHODS

CROSS REFERENCE TO RELATED APPLICATION

This application is a continuation of U.S. patent application Ser. No. 16/189,360, filed Nov. 13, 2018; which is a continuation of U.S. patent application Ser. No. 15/640,675, filed Jul. 3, 2017; which is a continuation of U.S. patent application Ser. No. 15/412,341, filed on Jan. 23, 2017, now U.S. Pat. No. 9,750,671, granted Sep. 5, 2017; which is a divisional of U.S. patent application Ser. No. 14/755,507, filed on Jun. 30, 2015, now U.S. Pat. No. 9,687,425, granted on Jun. 27, 2017, the entire disclosures of which are fully incorporated by reference.

FIELD OF THE INVENTION

The present disclosure generally relates to methods of manufacturing personal care compositions that include microcapsules.

BACKGROUND OF THE INVENTION

Personal care compositions have become a staple in the personal hygiene routine for many people. Personal care compositions can provide benefits to consumers such as by combating wetness, reducing malodor, and/or delighting the consumer with the scent of a fragrance. There is, however, room for improvement with respect to the longevity of the fragrance in personal care compositions.

SUMMARY OF THE INVENTION

A method of manufacturing an anhydrous personal care composition, the method comprising: combining a first process stream at a first temperature and a second process stream at a second temperature, wherein the first process stream comprises a material selected from the group consisting of a structurant, a solvent, and combinations thereof, and the second process stream comprises a plurality of microcapsules; wherein the second temperature does not exceed 80° C.

BRIEF DESCRIPTION OF THE DRAWINGS

FIG. 1 is a schematic diagram of a split stream manufacturing process.

DETAILED DESCRIPTION OF THE INVENTION

I. Definitions

As used herein, the following terms shall have the meaning specified thereafter:

"Ambient" refers to surrounding conditions at about one atmosphere of pressure, about 50% relative humidity, and about 25° C.

"Anhydrous" refers to compositions and/or components which are substantially free of water or free of water.

"Free of" means that the stated ingredient has not been added to the personal care composition. However, the stated ingredient may incidentally form as a byproduct or a reaction product of the other components of the personal care composition.

"Personal care composition" refers to compositions, including but not limited to, creams, gels, solid sticks, aerosols, and soft-solid sticks. For example, the personal care composition may be a composition such as a soft-solid deodorant, soft-solid antiperspirant, an invisible solid deodorant, an invisible solid antiperspirant, aerosol antiperspirant, fluid antiperspirant, body powder, or foot powder.

"Onset of crystallization" means the temperature at which a material crystallizes from a liquid solution. All melting points and onsets of crystallization referenced herein, unless otherwise specified, are measured by the well known technique of Differential Scanning calorimetry (DSC). For evaluation, a Perkin-Elmer 7 Series Thermal Analysis System Model DSC7 manufactured by Perkin-Elmer, Norwalk, Conn. is used.

"PMC" refers to microcapsules having a shell encapsulating a core material, where the core material includes at least one benefit agent.

"Soft solid" refers to a composition with a static yield stress of about 200 Pa to about 1,500 Pa after dispensing.

"Substantially free of" refers to about 2% or less, about 1% or less, or about 0.1% or less of a stated ingredient by weight of the personal care composition.

II. High Temperatures and Fragrance Release from Microcapsules

Initial tries to manufacture anhydrous personal care compositions that incorporated PMCs resulted in failures when the personal care compositions were made via a batch process. It was initially believed that there was an ingredient included within the personal care composition that was interfering with the PMCs. Several attempts were made to identify the incompatible ingredient, but such an ingredient was never identified.

It has been surprisingly discovered that the prolonged exposure of personal care compositions containing microcapsules to high levels of heat may result in a significant reduction in the release of the fragrance from the microcapsules. For reasons unknown, the exposure to high levels of heat (i.e. >40° C.) when manufacturing the personal care composition has been found to impact the amount of fragrance released into the headspace by the microcapsules.

The impact of high levels of heat was unexpected as for at least some of the microcapsules, for example the polyacrylate microcapsules used in the Examples herein, because the glass transition temperature of the microcapsules in many cases far exceeded that temperatures used in manufacturing the personal care compositions. In this regard, for microcapsules encapsulating a liquid, such as a liquid fragrance, the glass transition temperature of the microcapsules and the glass transition temperature of the shell of said microcapsule are typically about the same. For at least some of the microcapsules provided herein such as for the polyacrylate microcapsules, the microcapsules may have a shell with a glass transition temperature that is less than or equal to 75-150 degrees Celsius. Thus, although the glass transition temperature of the microcapsules exceeded the processing temperature for the manufacture of the personal care composition, exposure of the microcapsules to the high levels of heat still impacted the performance of the microcapsules. Without being bound by theory, it is believed that the high levels of heat during the manufacturing of the personal care composition may result in the extraction of the fragrance from the microcapsule over time.

The reduction in fragrance release upon exposure to high levels of heat was observed with microcapsules whose shell materials contained synthetic polymers and with microcapsules whose shell materials contained naturally-occurring polymers. Because prolonged exposure of personal care compositions to high temperatures is common during the production of many types of personal care compositions, including antiperspirant compositions, creating a process that substantially minimizes the amount of heat and the time of exposure to said heat is likely to improve the performance (i.e. fragrance release) of microcapsules in personal care compositions.

In this regard, Table 2 illustrates the effect of a prolonged exposure of personal care compositions containing PMCs to high temperatures when prepared using a batch process. Example A is a soft solid antiperspirant composition containing fragrance-loaded polyacrylate microcapsules, made using a batch process. Example B is an invisible solid, antiperspirant composition containing fragrance-loaded polyacrylate microcapsules, made using a batch process. Example D is a personal care composition containing fragrance-loaded polyacrylate microcapsules and cyclopentasiloxane, made by a batch process. Example E is a personal care composition containing fragrance-loaded polyacrylate microcapsules and dimethicone, made by a batch process. Example F is a personal care composition containing fragrance-loaded gelatin microcapsules and dimethicone, made by a batch process.

The results illustrated below in Table 2 were generated using the headspace test method described herein, with the following settings: manufacturer standard settings were used with a 10 second pump for Examples A, B, D, E and F. The analysis of Examples A and B was conducted using a 40° C. sensor temperature. The analysis of Examples D, E and F was conducted using a 60° C. sensor temperature. Each example was held at an elevated temperature for 72 hours. Examples A, B, and D were each held at 73° C. for 72 hours while Examples E and F were held at 75° C. for 72 hours. The percent decrease is calculated according to the following equation: ((Initial Headspace Value—72 Hour Headspace value)/Initial Headspace Value)*100%.

For Example A, exposure to 73° C. for 48 hours decreased the amount of fragrance released into the headspace from an initial headspace count of 12929 to a count of 6421. Exposure of Example A to 73° C. for 72 hours further decreased the amount of fragrance released into the headspace to a count of 4123. For Example B, exposure to 73° C. for 72 hours decreased the amount of fragrance released into the headspace from an initial headspace count of 8754 to a count of 1637. For Example D, exposure to 73° C. for 72 hours decreased the amount of fragrance released into the headspace from an initial headspace count of 55764 to a count of 21856. For Example E, exposure to 73° C. for 48 hours decreased the amount of fragrance released into the headspace from an initial headspace count of 30088 to a count of 13818. Exposure of Example E to 75° C. for 72 hours further decreased the amount of fragrance released into the headspace to a count of 11524. For Example F, exposure to 73° C. for 48 hours decreased the amount of fragrance released into the headspace from an initial headspace count of 22057 to a count of 9536. Exposure of Example F to 75° C. for 72 hours decreased the amount of fragrance released into the headspace from an initial headspace count of 22057 to a count of 11856. Additionally, exposure of a soft solid or invisible solid to 73° C. for 24 hours also resulted in decreases in the performance of microcapsules (data not shown). These data suggest that the prolonged exposure of a personal composition containing fragrance-loaded microcapsules to high temperatures (e.g. at least 72° C.) results in a reduction in the release of fragrance from the microcapsules. The data further suggests that microcapsules whose shell materials are made using synthetic polymers and microcapsules whose shell materials are made using naturally-occurring polymers are likely both susceptible to prolonged exposures to elevated temperatures during the manufacturing of the personal care composition.

TABLE 2

| | | | | peak area analyzed | | |
| --- | --- | --- | --- | --- | --- | --- |
| Example | Composition | PMC Type | Initial | 48 hr exposure | 72 hr exposure | Percent Decrease |
| A | Soft Solid | Polyacrylate | 12929 | 6421 | 4123 | 68.1% |
| B | Invisible Solid | Polyacrylate | 8754 | — | 1637 | 81.3% |
| D | Cyclopentasiloxane | Polyacrylate | 55764 | — | 21856 | 60.8% |
| E | Dimethicone | Polyacrylate | 30088 | 13818 | 11524 | 61.7% |
| F | Dimethicone | Gelatin | 22057 | 9536 | 11856 | 46.2% |

Table 3, below, illustrates the affect of a prolonged exposure of personal care compositions containing fragrance-loaded microcapsules to a range of temperatures ranging from 40° C. to 80° C. during a batch process. The results illustrated in Table 3 were generated using the headspace test method described herein, with the following settings: manufacturer standard settings were used with a 10 second pump and 60° C. sensor for Examples E and F. All Examples were held at the temperature indicated in Table 3 for 72 hours. The Percent decrease is calculated according to the following equation: ((Initial Headspace Value–72 Hour Headspace value)/Initial Headspace Value)*100%.

Referring to Table 3, Examples E and F were subjected to temperatures ranging from 40° C. to 80° C. The initial headspace values for Examples E and F were derived from samples prior to being subjected to elevated temperatures. As can be seen from Table 3, prolonged exposure to a temperature of at least 50° C. for 72 hours was sufficient to cause a decrease in the performance of Example E as demonstrated by the 21.6% decrease in the headspace counts. Prolonged exposure to a temperature of at least 55° C. for 72 hours was sufficient to cause a decrease in the performance of Example E and Example F as demonstrated by the 38.9% and 48.7% decrease, respectively, in the headspace counts. Prolonged exposure of Examples E and F to a temperature greater than 60° C. further decreased the performance of the microcapsules in said examples. These data suggest that the prolonged exposure of personal composition containing fragrance-loaded microcapsules to high temperatures (e.g. greater than 40° C.) results in a reduction in the release of fragrance from the microcapsules and that said reduction occurs for both microcapsules whose shell materials are made using synthetic polymers and for microcapsules whose shell materials are made using naturally-occurring polymers.

TABLE 3

| | % Decrease vs. initial headpspace value | |
|---|---|---|
| Temperature (° C.) | Example E (Percent Decrease) Polyacrylate PMC | Example F (Percent Decrease) Gelatin PMC |
| 40 | −3.4% | — |
| 50 | 21.6% | — |
| 55 | 38.9% | 48.7% |
| 60 | 28.6% | — |
| 70 | 56.7% | — |
| 75 | 62.0% | 46.2% |
| 80 | 46.6% | — |

Although it is not uncommon for personal care compositions to be subjected to temperatures greater than 40° C. for prolonged periods of time during the manufacturing process, the data illustrated in Tables 2 and 3 demonstrate that such temperatures may negatively impact the performance of fragrance-loaded microcapsules in such personal care compositions. The data shown in Table 4, generated using the headspace test method described herein, demonstrates at least two different ways of manufacturing a personal care composition containing fragrance-loaded microcapsules without significantly impairing the performance of the microcapsules.

TABLE 4

| Example | Initial | Held for 72 Hours at 73° C. |
|---|---|---|
| B | 8754 | 1637 |
| C | 7185 | — |

Referring to Table 4, Example B represents an invisible solid made by a batch process and Example C is an invisible solid, antiperspirant composition containing fragrance-loaded polyacrylate microcapsules made by a split stream process where the fragrance-loaded microcapsules were added via the second process stream, as described herein. Example B was subjected to 73° C. for one hour for 72 hours. Example B had an initial headspace count of 8754 after a one hour exposure to 73° C. Exposure of Example B to 73° C. for 72 hours decreased the head space count to 1637. In contrast, Example C had an initial head space count of 7185. These data suggest that while the batch process may be used to manufacture personal care compositions containing fragrance-loaded microcapsules, exposure to high levels of heat for extended periods of time during the process may impact the performance of the microcapsules in the personal care compositions. Further, it is likely that placing the fragrance-loaded microcapsules into the first process stream of the split stream process may also impact the performance of the microcapsules due to the prolonged exposure to high levels of heat.

To minimize the exposure of the microcapsules to high levels of heat during the manufacture of personal care compositions, the following are suggested improvements to existing methods:

1) Use of a split stream process, as described herein, where the PMCs are included within the second process stream.
2) Applying the concept of Late Point Product Differentiation described herein such as by adding the microcapsules to the personal care composition when the temperature of the personal care composition is less than 80° C., less than 70° C., less than 60° C., less than 55° C., or less than 50° C., but above the temperature at which point the personal care composition solidifies.
3) A batch process to produce personal care compositions containing PMCs may require monitoring the temperature of the holding tank containing the personal care composition to ensure the personal care composition is not subjected to temperatures that are shown above to impact the performance of the microcapsules. In some cases, the temperatures of the personal care composition should not be subject to temperatures greater than 60° C. for more than 72 hours when the microcapsules are polyacrylate microcapsule, and not subject to temperatures greater than 55° C. for more than 72 hours when the microcapsules' shell include gelatin. In some instances, it may not be desirable to exceed 55° C. for more than 24 hours.

Antiperspirant Active

Antiperspirant compositions may include an antiperspirant active suitable for application to human skin. The concentration of the antiperspirant active in the antiperspirant composition should be sufficient to provide the desired enhanced wetness protection. For example, the active may be present in an amount of from about 0.1%, about 0.5%, about 1%, or about 5%; to about 60%, about 35%, about 25% or about 20%, by weight of the antiperspirant composition. These weight percentages are calculated on an anhydrous metal salt basis exclusive of water and any complexing agents such as glycine, glycine salts, or other complexing agents.

An antiperspirant active may include any compound, composition, or other material having antiperspirant activity. Such actives may include astringent metallic salts, like inorganic and organic salts of aluminum, zirconium and zinc, as well as mixtures thereof. For example, the antiperspirant active may include zirconium-containing salts or materials, such as zirconyl oxyhalides, zirconyl hydroxyhalides, and mixtures thereof; and/or aluminum-containing salts such as, for example, aluminum halides, aluminum chlorohydrate, aluminum hydroxyhalides, and mixtures thereof.

1. Aluminum Salts

Aluminum salts useful herein may include those that conform to the formula:

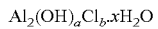

$Al_2(OH)_aCl_b \cdot xH_2O$ wherein a is from about 2 to about 5; the sum of a and b is about 6; x is from about 1 to about 6; where a, b, and x may have non-integer values. For example, aluminum chlorohydroxides referred to as "⅚ basic chlorohydroxide," wherein a is about 5 and "⅔ basic chlorohydroxide", wherein a=4 may be used.

A general description of these aluminum salts may be found in *Antiperspirants and Deodorants*, Cosmetic Science and Technology Series Vol. 20, 2$^{nd}$ edition, edited by Karl Laden. Mixtures of aluminum salts are described in British Patent Specification 1,347,950, filed in the name of Shin et al. and published Feb. 24, 1974.

2. Zirconium Salts

Zirconium salts useful herein may include those which conform to the formula:

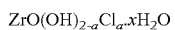

$ZrO(OH)_{2-a}Cl_a \cdot xH_2O$ wherein a is from about 1.5 to about 1.87; x is from about 1 to about 7; and wherein a and x may both have non-integer values. These zirconium salts are described in Belgian Patent 825,146, issued to Schmitz on Aug. 4, 1975. Useful to the present invention are zirconium salt complexes that additionally contain aluminum and glycine, commonly known as "ZAG complexes". These complexes may contain aluminum chlorohydroxide and zirconyl hydroxy chloride conforming to the above-described formulas. Examples of two such complexes include aluminum zirconium trichlorohydrex and aluminum zirconium tetrachlorohydrex.

Structurants

Personal care compositions may also include a structurant to help provide the personal care composition with the desired viscosity, rheology, texture and/or product hardness, or to otherwise help suspend any dispersed solids or liquids within the personal care composition. The term "structurant" may include any material known or otherwise effective in providing suspending, gelling, viscosifying, solidifying, or thickening properties to the personal care composition or which otherwise provide structure to the final product form. Non-limiting examples of structurants include, for example, gelling agents, polymeric or nonpolymeric agents, inorganic thickening agents, or viscosifying agents. Non-limiting examples of thickening agents include, for example, organic solids, silicone solids, crystalline or other gellants, inorganic particulates such as clays or silicas, or combinations thereof.

The concentration and type of the structurant selected for use in the personal care composition may vary depending upon the desired product form, viscosity, and hardness. The thickening agents suitable for use herein, may have a concentration range from about 0.1%, about 3%, or about 5%; to about 35%, about 20%, or about 10%, by weight of the personal care composition. Soft solids will often contain a lower amount of structurant than solid compositions. For example, a soft solid may contain from about 1.0% to about 9%, by weight of the composition, while a solid composition may contain from about 15% to about 25%, by weight of the personal care composition, of a structurant. This is not a hard and fast rule, however, as a soft solid product with a higher structurant value may be formed by, for example, shearing the product as it is dispensed from a package.

Non-limiting examples of suitable gelling agents include fatty acid gellants, salts of fatty acids, hydroxyl acids, hydroxyl acid gellants, esters and amides of fatty acid or hydroxyl fatty acid gellants, cholesterolic materials, dibenzylidene alditols, lanolinolic materials, fatty alcohols, triglycerides, sucrose esters such as SEFA behenate, inorganic materials such as clays or silicas, other amide or polyamide gellants, and mixtures thereof. Optionally, the microcapsules may be premixed with such gellants prior to incorporation into the personal care composition.

Suitable gelling agents include fatty acid gellants such as fatty acid and hydroxyl or alpha hydroxyl fatty acids, having from about 10 to about 40 carbon atoms, and ester and amides of such gelling agents. Non-limiting examples of such gelling agents include, but are not limited to, 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred gelling agents are 12-hydroxystearic acid, esters of 12-hydroxystearic acid, amides of 12-hydroxystearic acid and combinations thereof.

Other suitable gelling agents include amide gellants such as di-substituted or branched monoamide gellants, mono-substituted or branched diamide gellants, triamide gellants, and combinations thereof, including n-acyl amino acid derivatives such as n-acyl amino acid amides, n-acyl amino acid esters prepared from glutamic acid, lysine, glutamine, aspartic acid, and combinations thereof. Other suitable amide gelling agents are described in U.S. Pat. No. 5,429,816, issued Jul. 4, 1995, and U.S. Pat. No. 5,840,287, filed Dec. 20, 1996.

Still other examples of suitable gelling agents include fatty alcohols having at least about 8 carbon atoms, at least about 12 carbon atoms but no more than about 40 carbon atoms, no more than about 30 carbon atoms, or no more than about 18 carbon atoms. For example, fatty alcohols include but are not limited to cetyl alcohol, myristyl alcohol, stearyl alcohol and combinations thereof.

Non-limiting examples of suitable triglyceride gellants include tristearin, hydrogenated vegetable oil, trihydroxystearin (Thixcin® R, available from Rheox, Inc.), rape seed oil, castor wax, fish oils, tripalmitin, Syncrowax® HRC and Syncrowax® HGL-C(Syncrowax® available from Croda, Inc.).

Other suitable thickening agents include waxes or wax-like materials having a melt point of above 65° C., more typically from about 65° C. to about 130° C., examples of which include, but are not limited to, waxes such as beeswax, carnauba, bayberry, candelilla, montan, ozokerite, ceresin, hydrogenated castor oil (castor wax), synthetic waxes and microcrystalline waxes. The synthetic wax may be, for example, but not limited to, a polyethylene, a polymethylene, or a combination thereof. Some suitable polymethylenes may have a melting point from about 65° C. to about 75° C. Examples of some suitable polyethylenes include those with a melting point from about 60° C. to about 95° C. Other high melting point waxes are described in U.S. Pat. No. 4,049,792, Elsnau, issued Sep. 20, 1977.

Further structurants for use in the personal care compositions may include inorganic particulate thickening agents such as clays and colloidal pyrogenic silica pigments. For example, but not limited to, colloidal pyrogenic silica pigments such as Cab-O-Sil®, a submicroscopic particulated pyrogenic silica may be used. Other known or otherwise effective inorganic particulate thickening agents that are commonly used in the art may also be used in the personal care compositions described herein. Concentrations of particulate thickening agents may range, for example, from about 0.1%, about 1%, or about 5%; to about 35%, about 15%, about 10% or about 8%, by weight of the personal care composition.

Clay structurants include montmorillonite clays, non-limiting examples of which include bentonites, hectorites, and colloidal magnesium aluminum silicates. These and other clays may be hydrophobically treated, and when treated will generally be used in combination with a clay activator. Non-limiting examples of suitable clay activators include propylene carbonate, ethanol, and combinations thereof. When clay activators are present, the amount of clay activator may be in a range of from about 40%, about 25%, or about 15%; to about 75%, about 60%, or about 50%, by weight of the clay.

Surfactant

The personal care compositions may include a surfactant. A surfactant is generally present at a level of about 0.05% to about 5%, by weight of the personal care composition, but may contain, from about 0.5% to about 5.0%; from about 1.0% to about 4%; from about 1.5% to about 3.5%; from about 1.75% to about 2.5%; about 2%, or any combination thereof. The surfactant may have a HLB range of about 2 to about 14; about 6 to about 12; about 8 to about 10; or any combination thereof. The surfactant may be free of polyoxyethylene sorbitan fatty acids. The surfactant may comprise, for example, a $C_{20-40}$ Pareth-10. Another suitable surfactant is a nonionic ethoxylated linear alcohol with a carbon chain length of 20-40. Suitable surfactants include PERFORMATHOX™ 450 ethoxylate.

Anhydrous Liquid Carrier

Personal care compositions may also include anhydrous liquid carriers. The anhydrous liquid carrier may be present, for example, at concentrations ranging from about 10%, about 15%, about 20%, about 25%; to about 99%, about 70%, about 60%, or about 50%, by weight of the personal care composition. Such concentrations will vary depending upon variables such as product form, desired product hardness, and selection of other ingredients in the personal care composition. The anhydrous carrier may be any anhydrous carrier known for use in personal care compositions or otherwise suitable for topical application to the skin. For example, anhydrous carriers may include, but are not limited to, volatile and nonvolatile fluids.

A. Volatile Fluid

The personal care compositions may also include a volatile fluid such as a volatile silicone carrier. Volatile fluids are present, for example, at concentrations ranging from about 20% or from about 30%; to about 80%, or no about 60%, by weight of the personal care composition. The volatile silicone of the solvent may be cyclic, linear, and/or branched chain silicone. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976).

The volatile silicone may be a cyclic silicone. The cyclic silicone may have from about 3 silicone atoms, or from about 5 silicone atoms; to about 7 silicone atoms, or to about 6 silicone atoms. For example, volatile silicones may be used which conform to the formula:

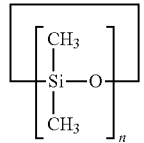

wherein n is from about 3, or from about 5; to about 7, or to about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

B. Non-Volatile Fluid

A non-volatile fluid may also be present, for example, at concentrations ranging from about 1%, from about 2%; to about 20%, or about 15%, by weight of the personal care composition.

1. Non-Volatile Organic Fluids

The non-volatile organic fluid may be present at concentrations ranging from about 1%, from about 2% but no more than about 20% or no more than about 15%, by weight of the personal care composition.

Non-limiting examples of nonvolatile organic fluids include, but are not limited to, mineral oil, PPG-14 butyl ether, isopropyl myristate, petrolatum, butyl stearate, cetyl octanoate, butyl myristate, myristyl myristate, C12-15 alkylbenzoate (e.g., Finsolv™), dipropylene glycol dibenzoate, PPG-15 stearyl ether benzoate and blends thereof (e.g. Finsolv TPP), neopentyl glycol diheptanoate (e.g. Lexfeel 7 supplied by Inolex), octyldodecanol, isostearyl isostearate, octododecyl benzoate, isostearyl lactate, isostearyl palmitate, isononyl/isononoate, isoeicosane, octyldodecyl neopentanate, hydrogenated polyisobutane, and isobutyl stearate. Many such other carrier liquids are disclosed in U.S. Pat. No. 6,013,248 (Luebbe et al.) and U.S. Pat. No. 5,968,489 (Swaile et al.).

2. Nonvolatile Silicone Fluids

The personal care composition may also include a nonvolatile silicone fluid. The non-volatile silicone fluid may be a liquid at or below human skin temperature, or otherwise in liquid form within a personal care composition, like an anhydrous antiperspirant composition, during or shortly after topical application. The concentration of the nonvolatile silicone may be from about 1%, from about 2%; to about 15%, about 10%, by weight of the personal care composition. Nonvolatile silicone fluids may include those which conform to the formula:

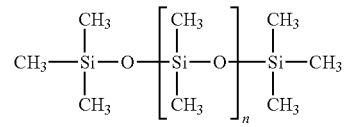

wherein n is greater than or equal to 1. These linear silicone materials may generally have viscosity values of from about 5 centistokes, from about 10 centistokes; to about 100,000 centistokes, about 500 centistokes, about 200 centistokes, or about 50 centistokes, as measured under ambient conditions.

Specific non limiting examples of suitable nonvolatile silicone fluids include Dow Corning 200, hexamethyldisiloxane, Dow Corning 225, Dow Corning 1732, Dow Corning 5732, Dow Corning 5750 (available from Dow Corning Corp.); and SF-96, SF-1066 and SF18(350) Silicone Fluids (available from G.E. Silicones).

Low surface tension non-volatile solvent may be also be used. Such solvents may be selected from the group consisting of dimethicones, dimethicone copolyols, phenyl trimethicones, alkyl dimethicones, alkyl methicones, and mixtures thereof. Low surface tension non-volatile solvents are also described in U.S. Pat. No. 6,835,373 (Kolodzik et al.).

Malodor Reducing Agent

The personal care composition may also include a malodor reducing agent. Malodor reducing agents include components other than the antiperspirant active within the personal care composition that act to eliminate the effect that body odor has on fragrance display. These agents may combine with the offensive body odor so that they are not detectable including and may suppress the evaporation of malodor from the body, absorb sweat or malodor, mask the malodor, and/or prevent/inhibit microbiological activity from odor causing organisms. The concentration of the malodor reducing agent within the personal care composition should be sufficient to provide such chemical or biological means for reducing or eliminating body odor.

Although the concentration will vary depending on the agent used, generally, the malodor reducing agent may be included within the personal care composition from about 0.05%, about 0.5%, or about 1%; to about 15%, about 10%, or about 6%, by weight of the personal care composition.

Malodor reducing agents may include, but are not limited to, pantothenic acid and its derivatives, petrolatum, menthyl acetate, uncomplexed cyclodextrins and derivatives thereof, talc, silica and mixtures thereof. Such agents may be used as described in U.S. Pat. No. 6,495,149, issued to Scavone, et al. and U.S. patent application 2003/0152539, filed Jan. 25, 2002 in the names of Scavone, et al.

For example, if panthenyl triacetate is used, the concentration of the malodor reducing agent may be from about 0.1% or about 0.25%; to about 3.0%, or about 2.0%, by weight of the personal care composition. Another example of a malodor reducing agent is petrolatum which may be included from about 0.10%, or about 0.5%; to about 15%, or about 10%, by weight of the personal care composition. A combination may also be used as the malodor reducing agent including, but not limited to, panthenyl triacetate and petrolatum at levels from about 0.1%, or 0.5%; to about 3.0%, or about 10%, by weight of the personal care composition. Menthyl acetate, a derivative of menthol that does not have a cooling effect, may be included from about 0.05%, or 0.01%; to about 2.0%, or about 1.0%, by weight of the personal care composition. The malodor reducing agent(s) may be in the form of a liquid or a semi-solid such that it does not contribute to product residue.

Microcapsules

The personal care compositions herein may include microcapsules. The microcapsules may be any kind of microcapsule disclosed herein or known in the art. The microcapsules may have a shell and a core material encapsulated by the shell. The core material of the microcapsules may include one or more fragrances. The shells of the microcapsules may be made from synthetic polymeric materials or naturally-occurring polymers. Synthetic polymers can be derived from petroleum oil, for example. Non-limiting examples of synthetic polymers include nylon, polyethylenes, polyamides, polystyrenes, polyisoprenes, polycarbonates, polyesters, polyureas, polyurethanes, polyolefins, polysaccharides, epoxy resins, vinyl polymers, polyacrylates, and mixtures thereof. Non-limiting examples of suitable shell materials include materials selected from the group consisting of reaction products of one or more amines with one or more aldehydes, such as urea cross-linked with formaldehyde or gluteraldehyde, melamine cross-linked with formaldehyde; gelatin-polyphosphate coacervates optionally cross-linked with gluteraldehyde; gelatin-gum Arabic coacervates; cross-linked silicone fluids; polyamine reacted with polyisocyanates; acrylate monomers polymerized via free radical polymerization, and mixtures thereof. Natural polymers occur in nature and can often be extracted from natural materials. Non-limiting examples of naturally occurring polymers are silk, wool, gelatin, cellulose, proteins, and combinations thereof.

The microcapsules may be friable microcapsules. A friable microcapsule is configured to release its core material when its shell is ruptured. The rupture can be caused by forces applied to the shell during mechanical interactions. The microcapsules may have a median volume weighted fracture strength of from about 0.1 MPa to about 25.0 MPa, when measured according to the Fracture Strength Test Method, or any incremental value expressed in 0.1 mega Pascals in this range, or any range formed by any of these values for fracture strength. As an example, the microcapsules may have a median volume weighted fracture strength of 0.5-25.0 mega Pascals (MPa), alternatively from 0.5-20.0 mega Pascals (MPa), 0.5-15.0 mega Pascals (MPa), or alternatively from 0.5-10.0 mega Pascals (MPa).

The microcapsules may have a median volume-weighted particle size of from 2 microns to 80 microns, from 10 microns to 30 microns, or from 10 microns to 20 microns, as determined by the Test Method for Determining Median Volume-Weighted Particle Size of Microcapsules described herein.

The microcapsules may have various core material to shell weight ratios. The microcapsules may have a core material to shell ratio that is greater than or equal to: 10% to 90%, 30% to 70%, 50% to 50%, 60% to 40%, 70% to 30%, 75% to 25%, 80% to 20%, 85% to 15%, 90% to 10%, and 95% to 5%.

The microcapsules may have shells made from any material in any size, shape, and configuration known in the art. Some or all of the shells may include a polyacrylate material, such as a polyacrylate random copolymer. For example, the polyacrylate random copolymer can have a total polyacrylate mass, which includes ingredients selected from the group including: amine content of 0.2-2.0% of total polyacrylate mass; carboxylic acid of 0.6-6.0% of total polyacrylate mass; and a combination of amine content of 0.1-1.0% and carboxylic acid of 0.3-3.0% of total polyacrylate mass.

When a microcapsule's shell includes a polyacrylate material, the polyacrylate material may form 5-100% of the overall mass, or any integer value for percentage in this range, or any range formed by any of these values for percentage, of the shell. As examples, the polyacrylate material may form at least 5%, at least 10%, at least 25%, at least 33%, at least 50%, at least 70%, or at least 90% of the overall mass of the shell.

The microcapsules may have various shell thicknesses. The microcapsules may have a shell with an overall thickness of 1-2000 nanometers, or any integer value for nanometers in this range, or any range formed by any of these values for thickness. As a non-limiting example, the microcapsules may have a shell with an overall thickness of 2-1100 nanometers.

The microcapsules may also encapsulate one or more benefit agents. The benefit agent(s) include, but are not limited to, one or more of chromogens, dyes, cooling sensates, warming sensates, fragrances, oils, pigments, in any combination. When the benefit agent includes a fragrance, said fragrance may comprise from about 2% to about 80%, from about 20% to about 70%, from about 30% to about 60% of a perfume raw material with a C log P greater than −0.5, or even from about 0.5 to about 4.5. In some examples, the fragrance encapsulated may have a C log P of less than 4.5, less than 4, or less than 3. In some examples, the microcapsule may be anionic, cationic, zwitterionic, or have a neutral charge. The benefit agents(s) can be in the form of solids and/or liquids. The benefit agent(s) include any kind of fragrance(s) known in the art, in any combination.

The microcapsules may encapsulate an oil soluble material in addition to the benefit agent. Non-limiting examples of the oil soluble material include mono, di- and tri-esters of $C_4$-$C_{24}$ fatty acids and glycerine; butyl oleate; hydrogenated castor oil; castor oil; mineral oil; capryllic triglyceride; vegetable oil; geranyl palmitate; silicone oil; isoproplyl myristate, soybean oil, hexadecanoic acid, methyl ester, isododecane, and combinations thereof, in addition to the encapsulated benefit agent. The oil soluble material may have a C log P about 4 or greater, at least 4.5 or greater, at least 5 or greater, at least 7 or greater, or at least 11 or greater.

The microcapsule's shell may comprise a reaction product of a first mixture in the presence of a second mixture comprising an emulsifier, the first mixture comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator. In some examples, said amine is an aminoalkyl acrylate or aminoalkyl methacrylate.

The microcapsules may include a core material and a shell surrounding the core material, wherein the shell comprises: a plurality of amine monomers selected from the group consisting of aminoalkyl acrylates, alkyl aminoalkyl acrylates, dialkyl aminoalykl acrylates, aminoalkyl methacrylates, alkylamino aminoalkyl methacrylates, dialkyl aminoalykl methacrylates, tertiarybutyl aminethyl methacrylates, diethylaminoethyl methacrylates, dimethylaminoethyl methacrylates, dipropylaminoethyl methacrylates, and mixtures thereof; and a plurality of multifunctional monomers or multifunctional oligomers.

Non-limiting examples of microcapsules include microcapsules that comprise a shell comprising an amine selected from the group consisting of diethylaminoethyl methacrylate, dimethylaminoethyl methacrylate, tertiarybutyl aminoethyl methacrylate; and combinations thereof; a core material encapsulated by said shell, said core material comprising about 10% to about 60% of a material selected from the group consisting of mono, di- and tri-esters of $C_4$-$C_{24}$ fatty acids and glycerine; isoproplyl myristate, soybean oil, hexadecanoic acid, methyl ester, isododecane, and combinations thereof, by weight of the microcapsule; and about 10% to about 90% of a perfume material, by weight of the microcapsule; wherein said microcapsules have a volume weighted fracture strength from 0.1 MPa to 25 MPa, preferably from 0.8 MPa to 20 MPa, more preferably from 1.0 MPa to 15 MPa; wherein said microcapsules have a median volume-weighted particle size from 10 microns to 30 microns.

Processes for making microcapsules are well known. Various processes for microencapsulation, and exemplary methods and materials, are set forth in U.S. Pat. Nos. 6,592,990; 2,730,456; 2,800,457; 2,800,458; 4,552,811; and U.S. 2006/0263518 A1.

The microcapsule may be spray-dried to form spray-dried microcapsules.

The personal care compositions may also include a parent fragrance and one or more encapsulated fragrances that may or may not differ from the parent fragrance. For example, the composition may include a parent fragrance and a non-parent fragrance. A parent fragrance refers to a fragrance that is dispersed throughout the composition and is typically not encapsulated when added to the composition. Herein, a non-parent fragrance refers to a fragrance that differs from a parent fragrance and is encapsulated with an encapsulating material prior to inclusion into a composition. Non-limiting examples of differences between a fragrance and a non-parent fragrance include differences in chemical make-up.

Some fragrances may be considered to be volatile and other fragrances may be considered to be or non-volatile, as described and defined herein. The term "non-volatile," as used herein, unless otherwise specified, refers to those materials that are liquid under ambient conditions and which have a measurable vapor pressure at 25° C. These materials typically have a vapor pressure less than about 0.01 mmHg, and an average boiling point typically greater than about 250° C. The term "volatile," as used herein, unless otherwise specified, refers to those materials that are liquid under ambient conditions and which have a measurable vapor pressure at 25° C. These materials typically have a vapor pressure greater than about 0.01 mmHg, more typically from about 0.02 mmHg to about 20 mmHg, and an average boiling point typically less than about 250° C., more typically less than about 235° C.

Other Fragrance Delivery Systems

The composition may also contain one or more other delivery systems for providing one or more benefit agents, in addition or in place of the microcapsules. The additional delivery system(s) may differ in kind from the microcapsules. For example, wherein the microcapsule are friable and encapsulate a fragrance, the additional delivery system may be an additional fragrance delivery system, such as a moisture-triggered fragrance delivery system. Non-limiting examples of moisture-triggered fragrance delivery systems include cyclic oligosaccharide, starch (or other polysaccharide material), or combinations thereof.

Starch

Examples of starches suitable for use can be made from raw starch, pregelatinized starch, modified starch derived from tubers, legumes, cereal and grains for example corn starch, wheat starch, rice starch, waxy corn starch, oat starch, cassava starch, waxy barley starch, waxy rice starch, sweet rice starch, amioca, potato starch, tapioca starch, and mixtures thereof. Further examples of modified starches may include hydrolyzed starch, acid thinned starch, starch having hydrophobic groups, such as starch esters of long chain hydrocarbons (C5 or greater), starch acetates, starch octenyl succinate, and mixtures thereof. An example of starch esters includes starch octenyl succinates.

Starch esters will typically have a degree of substitution in the range of from 0.01% to 10%. The hydrocarbon part of the modifying ester can be a C 5 to a C 16 carbon chain. As stated above, one example of a starch ester is octenyl succinate. The octenyl succinate (OSAN) can be a substituted waxy corn starch of various types such as 1) waxy starch, acid thinned and OSAN substituted, 2) blend of corn syrup solids: waxy starch, OSAN substituted and dextrinized, 3) waxy starch: OSAN substituted and dextrinised, 4) blend of corn syrup solids or maltodextrins with waxy starch: acid thinned OSAN substituted then cooked and spray dried, 5) waxy starch: acid thinned OSAN substituted then cooked and spray dried; and 6) the high and low viscosities of the above modifications (based on the level of acid treatment) can also be used. Mixtures of these, particularly mixtures of the high and low viscosity modified starches, are also suitable.

The term "hydrolyzed starch" refers to oligosaccharide-type materials that are typically obtained by acid and/or enzymatic hydrolysis of starches, like corn starch. A starch ester may be included in the starch water-mixture. The hydrolyzed starches, particularly for starch esters or mixture of starch esters, can have Dextrose Equivalent (DE) values of from 20 to 80, from 20 to 50, or even 25 to 38 DE. The DE value is a measure of the reducing equivalence of the hydrolyzed starch referenced to dextrose and expressed as a percent (on a dry basis). The higher the DE value, the more reducing sugars present. A method for determining DE values can be found in Standard Analytical Methods of the Member Companies of Corn Industries Research Foundation, 6th ed. Corn Refineries Association, Inc. Washington, D.C. 1980, D-52.

One example of a modified starch comprises a starch derivative containing a hydrophobic group, or both a hydrophobic and a hydrophilic group, which has been degraded by at least one enzyme capable of cleaving the 1,4 linkages of the starch molecule from the non-reducing ends to produce short chained saccharides to provide high oxidation resistance while maintaining substantially high molecular weight portions of the starch base. Such starches are described in EP-A-922 449.

Starches may also comprise monosaccharides such as glucose, disaccharides, trisaccharides, oligosaccharides, polysaccharides, and linear sugar alcohols such as mannite. As for the polysaccharides, mention may be made of starch, cellulose, chitin, chitosan, hemicellulose, pectin, pullulan, agar, alginic acid, carageenan, dextrin, trehalose, and the like.

Cyclic Oligosaccharide

As used herein, the term "cyclic oligosaccharide" means a cyclic structure comprising six or more saccharide units. The cyclic oligosaccharides may have six, seven, or eight saccharide units or mixtures thereof. It is common in the art to refer to six, seven and eight membered cyclic oligosaccharides as $\alpha$, $\beta$, and $\gamma$, respectively. The cyclic oligosaccharides that may be useful include those that are soluble in water, ethanol, or both water and ethanol. The cyclic oligosaccharides useful herein may have a solubility of at least about 0.1 g/100 ml, at 25° C. and 1 atm of pressure in either water, ethanol, or both water and ethanol. The personal care compositions disclosed herein may comprise from about 0.001% to about 40%, from about 0.1% to about 25%, from about 0.3% to about 20%, from about 0.5% to about 10%, or from about 0.75% to about 5%, by weight of the personal care composition, of a cyclic oligosaccharide. The personal care compositions disclosed herein may comprise from 0.001% to 40%, from 0.1% to 25%, from 0.3% to 20%, from 0.5% to 10%, or from 0.75% to 5%, by weight of the personal care composition, of a cyclic oligosaccharide.

The cyclic oligosaccharide may comprise any suitable saccharide or mixture of saccharides. Examples of suitable saccharides include, but are not limited to, glucose, fructose, mannose, galactose, maltose, and mixtures thereof. The cyclic oligosaccharide, or mixture of cyclic oligosaccharides, may be substituted by any suitable substituent or mixture of substituents. Herein, the use of the term "mixture of substituents" means that two or more different suitable substituents may be substituted onto one cyclic oligosaccharide. Suitable examples of substituents include, but are not limited to, alkyl groups, hydroxyalkyl groups, dihydroxyalkyl groups, carboxyalkyl groups, aryl groups, maltosyl groups, allyl groups, benzyl groups, alkanoyl groups, and mixtures thereof. These substituents may be saturated or unsaturated, straight or branched chain. For example, the substituents may include saturated and straight chain alkyl groups, hydroxyalkyl groups, and mixtures thereof. The alkyl and hydroxyalkyl substituents, for example, may also be selected from $C_1$-$C_8$ alkyl or hydroxyalkyl groups, alkyl and hydroxyalkyl substituents from $C_1$-$C_6$ alkyl or hydroxyalkyl groups, and alkyl and hydroxyalkyl substituents from $C_1$-$C_4$ alkyl or hydroxyalkyl groups. The alkyl and hydroxyalkyl substituents may be, for example, propyl, ethyl, methyl, and hydroxypropyl.

In addition to the substituents themselves, the cyclic oligosaccharides may have an average degree of substitution of at least 1.6, wherein the term "degree of substitution" means the average number of substituents per saccharide unit. For example, the cyclic oligosaccharides may have an average degree of substitution of less than about 2.8 or from about 1.7 to about 2.0. The average number of substituents may be determined using common Nuclear Magnetic Resonance techniques known in the art. Examples of cyclic oligosaccharides useful herein include cyclodextrins such as methyl-$\alpha$-cyclodextrins, methyl-$\beta$-cyclodextrins, hydroxypropyl-$\alpha$-cyclodextrins, hydroxypropyl-$\beta$-cyclodextrins, and mixtures thereof. The cyclodextrins may be in the form of particles. The cyclodextrins may also be spray-dried and may also be spray-dried particles. The cyclodextrins may also be complexed with a fragrance to form a complexed cyclodextrin.

Fragrances

The personal care compositions may include one or more fragrances. As used herein, "fragrance" is used to indicate any odoriferous material. Any fragrance that is cosmetically acceptable may be used in the personal care composition. For example, the fragrance may be one that is a liquid at room temperature. Generally, the fragrance(s) may be present at a level from about 0.01% to about 40%, from about 0.1% to about 25%, from about 0.25% to about 20%, or from about 0.5% to about 15%, by weight of the personal care composition.

A wide variety of chemicals are known as fragrances, including aldehydes, ketones, and esters. More commonly, naturally occurring plant and animal oils and exudates comprising complex mixtures of various chemical components are known for use as fragrances. Non-limiting examples of the fragrances useful herein include pro-fragrances such as acetal pro-fragrances, ketal pro-fragrances, ester pro-fragrances, hydrolyzable inorganic-organic pro-fragrances, and mixtures thereof. The fragrances may be released from the pro-fragrances in a number of ways. For example, the fragrance may be released as a result of simple hydrolysis, or by a shift in an equilibrium reaction, or by a pH-change, or by enzymatic release. The fragrances herein may be relatively simple in their chemical make-up, comprising a single chemical, or may comprise highly sophisticated complex mixtures of natural and synthetic chemical components, all chosen to provide any desired odor.

The fragrances may have a boiling point (BP) of about 500° C. or lower, about 400° C. or lower, or about 350° C. or lower. The BP of many fragrances are disclosed in *Perfume and Flavor Chemicals* (Aroma Chemicals), Steffen Arctander (1969). The C log P value of the fragrances may be about 0.1 or greater, about 0.5 or greater, about 1.0 or greater, and about 1.2 or greater. As used herein, "C log P" means the logarithm to the base 10 of the octanol/water partition coefficient. The C log P may be readily calculated from a program called "C LOG P" which is available from Daylight Chemical Information Systems Inc., Irvine Calif., USA. Octanol/water partition coefficients are described in more detail in U.S. Pat. No. 5,578,563.

Suitable fragrances are also disclosed in U.S. Pat. Nos. 4,145,184, 4,209,417, 4,515,705, and 4,152,272. Non-limiting examples of fragrances include animal fragrances such as musk oil, civet, castoreum, ambergris, plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, eucalyptus oil, verbena oil, mimosa extract, narcissus extract, carrot seed extract, jasmine extract, olibanum extract, rose extract, and mixtures thereof.

Other examples of suitable fragrances include, but are not limited to, chemical substances such as acetophenone, adoxal, aldehyde C-12, aldehyde C-14, aldehyde C-18, allyl caprylate, ambroxan, amyl acetate, dimethylindane derivatives, α-amylcinnamic aldehyde, anethole, anisaldehyde, benzaldehyde, benzyl acetate, benzyl alcohol and ester derivatives, benzyl propionate, benzyl salicylate, borneol, butyl acetate, camphor, carbitol, cinnamaldehyde, cinnamyl acetate, cinnamyl alcohol, cis-3-hexanol and ester derivatives, cis-3-hexenyl methyl carbonate, citral, citronnellol and ester derivatives, cumin aldehyde, cyclamen aldehyde, cyclo galbanate, damascones, decalactone, decanol, estragole, dihydromyrcenol, dimethyl benzyl carbinol, 6,8-dimethyl-2-nonanol, dimethyl benzyl carbinyl butyrate, ethyl acetate, ethyl isobutyrate, ethyl butyrate, ethyl propionate, ethyl caprylate, ethyl cinnamate, ethyl hexanoate, ethyl valerate, ethyl vanillin, eugenol, exaltolide, fenchone, fruity esters such as ethyl 2-methyl butyrate, galaxolide, geraniol and ester derivatives, helional, 2-heptonone, hexenol, α-hexylcinnamic aldehyde, hydroxycitrolnellal, indole, isoamyl acetate, isoeugenol acetate, ionones, isoeugenol, isoamyl iso-valerate, iso E super, limonene, linalool, lilial, linalyl acetate, lyral, majantol, mayol, melonal, menthol, p-methylacetophenone, methyl anthranilate, methyl cedrylone, methyl dihydrojasmonate, methyl eugenol, methyl ionone, methyl-α-naphthyl ketone, methylphenylcarbinyl acetate, mugetanol, γ-nonalactone, octanal, phenyl ethyl acetate, phenyl-acetaldehyde dimethyl acetate, phenoxyethyl isobutyrate, phenyl ethyl alcohol, pinenes, sandalore, santalol, stemone, thymol, terpenes, triplal, triethyl citrate, 3,3,5-trimethylcyclohexanol, γ-undecalactone, undecenal, vanillin, veloutone, verdox, and mixtures thereof.

Other Materials

The personal care compositions may also include other materials known for use in antiperspirant, deodorant or other personal care products, including those materials that are known to be suitable for topical application to skin. Non-limiting examples include dyes or colorants, emulsifiers, distributing agents, pharmaceuticals or other topical actives, skin conditioning agents or actives, deodorant agents, antimicrobials, preservatives, surfactants, processing aides such as viscosity modifiers and wash-off aids.

III. Methods of Use

The personal care compositions including an antiperspirant active may be applied topically to the underarm or other suitable area of the skin in an amount effective to reduce or inhibit perspiration wetness. The personal care compositions may be applied, for example, in an amount ranging from at least about 0.1 gram to about 20 grams, to about 10 grams, or to about 1 gram. The personal care composition may also be applied to the underarm at least about one or two times daily, preferably once daily, to achieve effective antiperspirant reduction or inhibition over an extended period or in an amount such that the fragrance applied is noticeable by the user.

The personal care composition may also be applied every other day, or every third or fourth day, and then optionally to supplement application on off-days with other personal care compositions such as deodorants and/or conventional antiperspirant formulations.

Personal care compositions may be applied to skin, wherein the volatile anhydrous carrier leaves behind a skin-adhering polymer and active-containing film. This film is positioned over the sweat ducts and resists flaking and/or rub-off, thereby being present through multiple perspiration episodes.

IV. Methods of Manufacturing

The personal care composition may be prepared by any known or otherwise effective technique, suitable for providing the personal care composition of the desired form while incorporating the teachings herein. Many such techniques are described in the antiperspirant/deodorant formulation arts for the described product forms. A few non-limiting examples are provided herein.

Personal care compositions may be made by a batch process. This process generally involves adding all of the raw materials (except active and perfume) to a mix tank, heating the materials to a temperature to melt the structurants and other higher melt point ingredients, and holding it at that temperature until the appropriate ingredients are melted. This heating step may involve temperatures of, for example, 80° C. or more, and it may take from 45 minutes to an hour for the ingredients to melt. At this point, the batch is cooled to 70-75° C. and the active and fragrances may be added to the tank. The personal care composition is usually mixed at the temperature of 70-75° C. for at least 15 minutes (and sometimes held at 70-75° C. for 24-72 hours) before being cooled to 50-55° C. and poured into, for example, canisters. Typically, the personal care composition is kept at or above the temperature that allows the personal care composition to be in a mobile state as to allow for transfer of the personal care composition from the main mix tank to individual canisters. In some cases, the personal care composition during the batch process remains in a molten state for a long period of time and may be kept at temperatures that impact the performance of the microcapsules.

A batch process to produce personal care compositions containing PMCs may require monitoring the temperature of the holding tank containing the personal care composition to ensure the personal care composition is not subjected to temperatures that are shown herein to impact the performance of the microcapsules. In this regard, the temperatures of the personal care composition containing the microcapsules should not be subjected to temperatures greater than 60° C. for more than 72 hours when the microcapsules are polyacrylate microcapsule, and not subject to temperatures greater than 55° C. for more than 72 hours when the microcapsules' shell include gelatin. In some instances, it may not be desirable to subject the personal care composition containing microcapsules to temperatures exceeding 55° C. for more than 24 hours. In some examples, the personal care composition including PMCs may be subjected to temperatures ranging from 40° C. to 80° C. for one hour or less. In some examples, the personal care composition including PMCs may be subjected to temperatures ranging from 40° C. to 60° C. for less than 72 hours.

Another method of manufacturing the personal compositions described herein includes a split stream method. This method is described in more detail below. Referring to FIG. 1, a non-limiting example of a suitable manufacturing method is shown. The method 100 combines at least two process streams, a first process stream 102 having a first temperature and second process stream 104 having a second temperature lower than the first temperature, within a mixing chamber 106. Due to the differences in temperature, the first process stream 102 may also be referred to as the hot stream, while the second process stream 104 may be referred to as the cold stream. As shown in FIG. 1, the first process stream 102 ingredients are mixed in a batch tank 108 while the second process stream 104 ingredients are mixed in separate batch tank 110. Conventional equipment, such as, for example, pumps 112 can be used to facilitate movement of the first and second process streams 102, 104 towards and into a mixing chamber 106.

The first process stream 102 may contain, for example, one or more structurants (e.g., a wax) melted in a solvent, and a surfactant which are held above the full melting point of the one or more waxes. The solvent of the first process stream 102 may be any material that is liquid at the holding temperature of the hot process stream 102 and that can essentially completely dissolve the wax structurant. The solvent may be selected from any of the previously described liquid carriers. In some instances, the solvent comprises a silicone fluid, such as cyclomethicone and/or dimethicone (also referred to as polydimethylsiloxane).

The first process stream 102 is preferably heated to a temperature sufficient to melt the one or more waxes in the solvent. In some examples, the temperature of the first process stream 102 is from about 65° C., 70° C., 75° C. or 80° C. to about 130° C., 120° C., 110° C., 100° C. or 90° C. within the tank 108 or a static mixer used to combine the ingredients of the first process stream 102. In some instances where the waxes are selected from the group consisting of stearyl alcohol, hydrogenated castor oil, ozokerite, synthetic wax, tribehenin, or C18-36 triglyceride and mixtures thereof, the temperature of the first process stream within the tank 108 (or static mixer), is from about 75° C. to about 95° C. or from about 80° C. to about 95° C.

A second process stream 104 may contain the balance of the liquid carriers, an antiperspirant active and any heat-sensitive components. The step of forming a second process stream can involve mixing an antiperspirant active, as described herein, and a solvent and optionally a heat sensitive component in the second batch tank 110 or a static mixer. The second stream 104 has a second temperature $T_c$ that is lower than the temperature $T_h$. Preferably, the second batch tank and the temperature $T_c$ are at ambient, although it may be provided at other temperatures such as at least about 20°, 50° or 70° C. lower than the temperature $T_h$. In instances where the waxes incorporated into the first process stream are selected from the group consisting of stearyl alcohol, hydrogenated castor oil, ozokerite, and mixtures thereof, the temperature of the second process stream within the tank 110 (or static mixer), is from about 20° C. to about 40° C. or from about 20° C. to about 30° C.

The second process stream 104 may include a liquid emollient or solvent, which may be selected from the various liquid carriers described above. A few non-limiting examples include mineral oil; PPG-14 butyl ether; isopropyl myristate; petrolatum; butyl stearate; cetyl octanoate; butyl myristate; myristyl myristate; C12-15 alkylbenzoate (e.g., Finsolv™); octyldodecanol; isostearyl isostearate; octododecyl benzoate; isostearyl lactate; isostearyl palmitate; isobutyl stearate; dimethicone, and any mixtures thereof.

The second process stream 104 may also optionally comprise any heat sensitive component that could chemically degrade or deteriorate or react with components of the antiperspirant composition at elevated temperatures or corrode metal process equipment at elevated storage temperatures.

The second process stream 104 may also include fragrance-loaded microcapsules. In some examples, the temperature of the second process stream within the tank 110 (or static mixer), is less than less than 75° C., less than 70° C., less than 60° C., less than 50° C. but greater than 0° C. In some examples, the second process stream 104 including the fragrance-loaded microcapsules may be at about 20° C. to about 40° C. In some examples, the second process stream 104 including the fragrance-loaded microcapsules does not exceed 80° C. In some examples, the microcapsules may be combined with at least one of an anhydrous liquid carrier and gelling agent prior to incorporation into the second process stream 104. In some examples, the microcapsules may be in the form of a powder with a water content of less than 15% by weight of the powder when the microcapsules are added to the second process stream 104. To produce said powder, the microcapsules may be dried from a slurry including greater than 15% water by centrifugation, batch or pressure filtration, tray drying, oven drying, spray drying, or any other form of drying.

The first process stream 102 and the second process stream 104 are combined in, or just prior to entering, the mixing chamber 106. The mixing chamber 106 may comprise a pipe, or any other suitable arrangement capable of receiving both the first process stream 102 and the second process stream 104 therein so that the streams are combined therein with sufficient turbulence to cause thorough mixing and heat transfer. By controlling the ratio of the first process stream 102 to the second process stream 104 at the mixing chamber 106, it is possible to control the temperature $T_e$ of the mixture exiting the mixing chamber 106. The mixing chamber 106 may be a small void space containing static baffles 114 or other physical structure arranged to enable substantial and/or thorough mixing and heat transfer between the first and second streams 102, 104. The first and second process streams 102, 104 may be introduced into the mixing chamber 106 in an opposed manner, one example of which is shown in FIG. 1, where the streams enter the mixing chamber at about 180° C. apart so that impaction of streams may significantly enhance their rapid mixing. While the first and second process streams 102, 104 are shown entering the mixing chamber in an opposed manner, it will be appreciated that other arrangements may be utilized.

Upon exiting the mixing chamber 106, the mixture flows to an injector 120, which may take the form of piston pump, which pushes a volume of the hot mixture into a dispensing package. The injector 120 has a nozzle 122 having an exit opening through which the mixture is ejected or essentially poured or cast into the dispensing package at atmospheric pressure. Since the mixture upon exiting the nozzle 122 is still hot and has a look and consistency similar to milk, the pressure used to dispense the mixture from the nozzle can be very low (e.g. 10 psig, 5 psig, 4 psig or even 2 psig or less), although it is contemplated that other pressures within the injector 120 might be utilized if desired. In some instances, the mixture is able to self level within the dispensing package prior to solidifying. In some instances, only a single mixture or casting step is utilized to fill the dispensing package in order to form a single phase solid stick antiperspirant composition.

Dispensing packages 125 may be maneuvered into position for filling by any means known in the art, including a conveyor 130. The dispensing packages 125 may be filled by top or bottom filling, as known in the art. A description of some examples of top and bottom filling processes is provided in commonly assigned USPN 2013/170886. The antiperspirant compositions cool within the dispensing package to ambient temperature to thereby form a solid stick antiperspirant composition.

The step of combining the at least one first process stream and the at least one second process stream together involves combining the streams in such a manner which may cause substantially complete mixing and heat transfer between the first process stream and the second process stream in a very short time period. The time period during which such mixing and heat transfer occur may be less than 3 seconds, more specifically less than 1 second, although longer mix times may also be used.

As discussed above, the temperature $T_e$ of the mixture exiting the mixing chamber 106 is preferably still hot. In some instances, the mixture exiting the mixing chamber may be from 10° C. to 15° C. or more above the onset of crystallization of the solid stick antiperspirant composition. In some instances, the mixture upon exiting the nozzle 122 may have an exit temperature from about 55° C. to about 60° C. or more. The mixture cools within the dispensing package, at which point one or more of the structurants may begin to crystallize. Preferably, complete mixing of the first process stream and the second process stream occurs within 3.5 inches, 2 inches or 1 inch of the where the first process stream and the second process stream enter the mixing chamber 106.

The temperature of the first process stream, the second process stream, and the resulting combined, product stream can be measured by any method known in the art. The temperature of the first process stream $T_h$ and the temperature of the second process stream $T_c$ can be measured just before the two streams enter the mixing chamber 106 or otherwise combine; and the temperature $T_e$ of the mixture can be measured right after the first and second process streams have been combined and exit the mixing chamber.

While the split stream method is described herein with regard to two process streams, it will be appreciated that the process is not limited to mixing just two process streams; one skilled in the art will understand that each of the first and second process streams may comprise several first and second process streams. Put another way, the present invention contemplates mixing multiple first process streams and multiple second process streams.

Late Point Product Differentiation

Late point product differentiation may also be utilized for maintaining the efficacy of the PMCs in the personal care composition. Late point product differentiation involves deferring when the end-product acquires its unique identities. With regards to the addition of microcapsules, this may involve the addition of the microcapsules into the finished product stream as the finished product stream is transferred from a larger, making system tank, into a smaller surge/holding tank, prior to dispensing into one or more canisters. The product temperature, upon incorporation of the microcapsules, may be decreased to a temperature below 75° C. or that temperature that promotes the degradation of the performance of the microcapsules. Non-limiting examples include adding the microcapsules to the personal care composition when the temperature of the personal care composition is less than 80° C., less than 70° C., less than 60° C., less than 55° C., or less than 50° C., but above the temperature at which point the personal care composition solidifies, usually in the range of 20–50° C. The microcapsules may be incorporated via a high speed disperser, which generates a vacuum to draw the microcapsules into the fluid flow-path. Complete homogenization of the microcapsule-containing finished product may then occur in the disperser prior to entering the surge/holding tank. Product temperature may be maintained in the surge tank below that which promotes the degradation of the microcapsules. The product may then be dispensed into individual canisters and control-cooled to generate the product's characteristics and attributes, thus minimizing the microcapsules exposure to elevated temperatures.

V. Headspace Test Method

Sample Preparation

1. For each personal care composition to be tested, prepare at least one Professional Aerosol Testing cardboard blotter card of 7.6×12.7 cm size, available from Orlandi Inc. (Farmingdale, N.Y., USA). (Additionally, prepare one 'control blotter' for fragrance(s) to be tested and tracked). Between 0.23-0.27 g of finished product composition should be applied to the blotter cards for sampling.
Before applying the personal care composition to the blotter cards, prepare or prime the dispensing device according to package directions. For a cream/conditioning/semi-solid product, expose the product until the finished product is seen coming through all dispensing holes in the devices' application surface, then wipe the application surface clean with a paper towel. For an invisible solid product, expose the product until the top rounded dome of the stick is fully exposed and then remove the exposed dome from the stick with a cutting wire by sliding across top of packaging, to achieve a flat surface on the stick of product. For fluids, powders, and aerosols, proceed to next step.
2. Pre-weigh each blotter card with an analytical balance. Apply the personal care composition evenly to the inner part of the blotter (leaving a 1.3 cm wide zone without product around the outside edge of the blotter card). This may involve spraying or pipetting, for example, depending on the state of the product (e.g. gas or liquid). Continue applying until between 0.23-0.27 g of the personal care composition is applied, using a balance to determine the weight. For invisible solid products, expose the cleanly cut stick surface until approximately 0.3 cm of the finished product is exposed above the packaging material, then apply the personal care composition evenly in a circular motion to the inner part of the blotter card, leaving a 1.3 cm wide zone without product around the outside edge of the blotter card. Continue applying until 0.23-0.27 g of the personal care composition is applied, using the balance to determine the weight. If the personal care composition does not appear evenly distributed across the application area upon visual evaluation, dispose of the blotter card and repeat the application process with a new card.
3. Repeat steps 1 and 2 for each personal care composition to be sampled.
4. Once all blotter cards have been prepared for each personal care composition to be sampled, lay the cards out on paper towels or other substrate with finished product side exposed overnight (18-24 hours) before conducting the zNose evaluation.
5. After the drydown period, roll each blotter card into a cylinder shape across the long axis of the card and put into a 207 mL clear polyethylene terephthalate disposable beverage cup with lid, such as available from Solo Cup Company (Lake Forest, Ill., USA). Arrange the card so the finished product side of the blotter is facing the inside of the cup. Close the lid. Repeat for all blotter cards. Samples are now prepped and in a controlled headspace ready for evaluation zNose Evaluation 1. Prepare the 7100 Benchtop zNose Fast-GC Analyzer (Model # MEA007100 with MicroSenseESTCal System Software version 5.44.28) with DB-624 column, or equivalent, as available from Electronic Sensor Technology Inc. (Newbury Park, Calif., USA), for evaluations, as defined in manufacturer's instructions.

2. Turn on zNose and perform daily cleaning steps. zNose is clean and operational when all 'peaks' are below 100 counts per mfr instructions.
3. Ensure 'Test Settings' are set according to the following:
   a. Sensor: 60° C. for fluids (40° C. for all else including Finished Product Soft Solid/Invisible Solid)
   b. Column: 40° C.
   c. Valve: 145° C.
   d. Inlet: 200° C.
   e. Trap: 200° C.
   f. Pump Time: 10 seconds
4. Once the test settings match the above requirements, calibrate the zNose with a n-alkanes standard. This will ensure zNose is operating according to manufacturer standard.
5. Once cleaned and calibrated, create a new alarm file. The new alarm file will contain no tagged peaks. Remove 'control blotter' from the cup then fold the card in half with the finished product application side on the inside. Using both hands, rub the outside of the folded card with the force required to break an egg, using a back and forth motion ten times, to cover the whole of one side of the folded card. Return the card to its cup, and re-seal. Run 'control blotter' from Step 1 according to manufacturer instructions. Tag all fragrance peaks below 1200 KI (Kovats Index). If no 'control blotter' is available for fragrance to be tested, all peaks (including baseline peaks from composition and peaks >1200 KI) must be tracked
6. Sampling order should be selected at random from all the samples to be tested.
7. For each cup to be sampled, remove blotter from the cup then fold the card in half with the finished product application side on the inside. Using both hands, rub the outside of the folded card with the force required to break an egg, using a back and forth motion ten times, to cover the whole of one side of the folded card. Return the card to its respective cup, and re-seal. Then immediately analyze said cup on the zNose with one run according to the manufacturer's instructions. After analysis, run a cleaning by bubbling methanol for 10 seconds. Repeat until all cups tested.
8. Once all cups have been tested, transfer all data to a spreadsheet and sum the total area under all peaks associated with the fragrance (or sum all peaks including baseline peaks if no 'control blotter' was tested).
9. For each cup tested, the analyses will result in a total fragrance peak area <1200 KI measurement by summing all tagged fragrance peaks <1200 KI in a new column. (If multiple replicates tested, calculate the average of all replicates, standard deviation, and % Relative Standard Deviation (% RSD)). The average of all replicates is the Total fragrance peak area <1200 KI for each respective personal care composition. If no control blotter was available to tag fragrance peaks, sum all of the peaks in a new column for tracking.
10. Each personal care composition should have a total fragrance peak area <1200 KI (or total peak area for personal care compositions without 'control blotters').

VI. Static Yield Stress/High Shear Viscosity

To determine static stress yield values for the personal care compositions herein, a two-part test may be conducted. First, a controlled stress ramp may ramp up linearly, and may measure a shear rate at each point of stress. In the second part of the two-part test, a controlled shear rate ramp may be linearly increased and shear stress may be measured. A rheological model may be used to fit the data in both segments of the test, and a value may be determined from the rheological model for both segments.

Personal care compositions are collected after they have been dispensed through their consumer use package and may be analyzed using a rheometer. In particular, the rheometer may be a Thermo Scientific Haake RheoStress 600 (available from TA Instruments, New Castle, Del., U.S.A) and data collection and analysis may be performed using rheology software, which may be RheoWin Software Version 2.84 or greater.

To prepare product samples, each product sample may be conditioned at about 23° C. until rheological properties may stabilize. An incubation period may be specified for each type of antiperspirant soft solid composition.

To operate the rheometer, parallel plates may be installed, and using the rheology software, a zero point for a gap between the parallel plates may be determined. A sufficient amount of the product sample may be loaded to ensure that entire serrated portions of the parallel plates may be in contact with the product sample once the product sample may be in a measurement position. A spatula may be used to carefully scrape dispensed product onto the serrated portion of a base plate. Once the product may be loaded, the rheology software may be used to move the parallel plates. A controlled stress ramp may be conducted followed by a controlled shear rate ramp.

Next, the rheology software may be used to determine shear yield stress values based on the controlled stress ramp and the controlled shear rate ramp. Data from the rheology test may be plotted as viscosity (Pa-s) on a log scale versus linear applied stress (Pa). "Static yield stress" refers to a point in a stress sweep analysis of a product at which point the rheometer is first capable of measuring product viscosity. The static yield stress is extrapolated from the data from a flow region along a shear rate measurement within 50-500 1/s.

VII. Fracture Strength Test Method

One skilled in the art will recognize that various protocols may be constructed for the extraction and isolation of microcapsules from finished products, and will recognize that such methods require validation via a comparison of the resulting measured values, as measured before and after the microcapsules' addition to and extraction from the finished product. The isolated microcapsules are then formulated in de-ionized (DI) water to form a slurry for characterization.

To calculate the percentage of microcapsules which fall within a claimed range of fracture strengths, three different measurements are made and two resulting graphs are utilized. The three separate measurements are namely: i) the volume-weighted particle size distribution (PSD) of the microcapsules; ii) the diameter of at least 10 individual microcapsules within each of 3 specified size ranges, and; iii) the rupture-force of those same 30 or more individual microcapsules. The two graphs created are namely: a plot of the volume-weighted particle size distribution data collected at i) above; and a plot of the modeled distribution of the relationship between microcapsule diameter and fracture-strength, derived from the data collected at ii) and iii) above. The modeled relationship plot enables the microcapsules within a claimed strength range to be identified as a specific region under the volume-weighted PSD curve, and then calculated as a percentage of the total area under the curve.

a.) The volume-weighted particle size distribution (PSD) of the microcapsules is determined via single-particle optical sensing (SPOS), also called optical particle counting (OPC), using the AccuSizer 780 AD instrument, or equivalent, and the accompanying software CW788 version 1.82 (Particle Sizing Systems, Santa Barbara, Calif., U.S.A.). The instrument is configured with the following conditions and selections: Flow Rate=1 ml/sec; Lower Size Threshold=0.50 μm; Sensor Model Number=LE400-05SE; Autodilution=On; Collection time=120 sec; Number channels=512; Vessel fluid volume=50 ml; Max coincidence=9200. The measurement is initiated by putting the sensor into a cold state by flushing with water until background counts are less than 100. A capsule slurry, and its density of particles is adjusted with DI water as necessary via autodilution to result in particle counts of at least 9200 per ml. During a time period of 120 seconds the suspension is analyzed. The resulting volume-weighted PSD data are plotted and recorded, and the values of the mean, $5^{th}$ percentile, and $90^{th}$ percentile are determined.

b.) The diameter and the rupture-force value (also known as the bursting-force value) of individual microcapsules are measured via a computer-controlled micromanipulation instrument system which possesses lenses and cameras able to image the microcapsules, and which possesses a fine, flat-ended probe connected to a force-transducer (such as the Model 403A available from Aurora Scientific Inc, Canada, or equivalent), as described in: Zhang, Z. et al. (1999) "Mechanical strength of single microcapsules determined by a novel micromanipulation technique." *J. Microencapsulation*, vol 16, no. 1, pages 117-124, and in: Sun, G. and Zhang, Z. (2001) "Mechanical Properties of Melamine-Formaldehyde microcapsules." *J. Microencapsulation*, vol 18, no. 5, pages 593-602, and as available at the University of Birmingham, Edgbaston, Birmingham, UK.

c.) A drop of the microcapsule suspension is placed onto a glass microscope slide, and dried under ambient conditions for several minutes to remove the water and achieve a sparse, single layer of solitary particles on the dry slide. Adjust the concentration of microcapsules in the suspension as needed to achieve a suitable particle density on the slide. More than one slide preparation may be needed.

d.) The slide is then placed on a sample-holding stage of the micromanipulation instrument. Thirty or more microcapsules on the slide(s) are selected for measurement, such that there are at least ten microcapsules selected within each of three pre-determined size bands. Each size band refers to the diameter of the microcapsules as derived from the Accusizer-generated volume-weighted PSD. The three size bands of particles are: the Mean Diameter +/−2 μm; the $5^{th}$ Percentile Diameter+/−2 μm; and the $90^{th}$ Percentile Diameter +/−2 μm. Microcapsules which appear deflated, leaking or damaged are excluded from the selection process and are not measured.

e.) For each of the 30 or more selected microcapsules, the diameter of the microcapsule is measured from the image on the micromanipulator and recorded. That same microcapsule is then compressed between two flat surfaces, namely the flat-ended force probe and the glass microscope slide, at a speed of 2 μm per second, until the microcapsule is ruptured. During the compression step, the probe force is continuously measured and recorded by the data acquisition system of the micromanipulation instrument.

f.) The cross-sectional area is calculated for each of the microcapsules, using the diameter measured and assuming a spherical particle ($\pi r^2$, where r is the radius of the particle before compression). The rupture force is determined for each sample by reviewing the recorded force probe measurements. The measurement probe measures the force as a function of distance compressed. At one compression, the microcapsule ruptures and the measured force will abruptly stop. This maxima in the measured force is the rupture force.

g.) The Fracture Strength of each of the 30 or more microcapsules is calculated by dividing the rupture force (in Newtons) by the calculated cross-sectional area of the respective microcapsule.

h.) On a plot of microcapsule diameter versus fracture-strength, a Power Regression trend-line is fit against all 30 or more raw data points, to create a modeled distribution of the relationship between microcapsule diameter and fracture-strength.

i.) The percentage of microcapsules which have a fracture strength value within a specific strength range is determined by viewing the modeled relationship plot to locate where the curve intersects the relevant fracture-strength limits, then reading off the microcapsule size limits corresponding with those strength limits. These microcapsule size limits are then located on the volume-weighted PSD plot and thus identify an area under the PSD curve which corresponds to the portion of microcapsules falling within the specified strength range. The identified area under the PSD curve is then calculated as a percentage of the total area under the PSD curve. This percentage indicates the percentage of microcapsules falling with the specified range of fracture strengths.

VIII. Examples

The following examples are given solely for the purpose of illustration and are not to be construed as limiting the invention, as many variations thereof are possible.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

EXAMPLE 1

Nonionic Microcapsules

An oil solution, consisting of 75 g Fragrance Oil scent A, 75 g of Isopropyl Myristate, 0.6 g DuPont Vazo-52, and 0.4 g DuPont Vazo-67, is added to a 35° C. temperature controlled steel jacketed reactor, with mixing at 1000 rpm (4 tip, 2" diameter, flat mill blade) and a nitrogen blanket applied at 100 cc/min. The oil solution is heated to 75° C. in 45 minutes, held at 75° C. for 45 minutes, and cooled to 60° C. in 75 minutes.

A second oil solution, consisting of 37.5 g Fragrance Oil, 0.25 g tertiarybutylaminoethyl methacrylate, 0.2 g 2-carboxyethyl acrylate, and 10 g Sartomer CN975 (hexafunctional urethane-acrylate oligomer) is added when the first oil solution reached 60° C. The combined oils are held at 60° C. for an additional 10 minutes.

Mixing is stopped and a water solution, consisting of 56 g of 5% active polyvinyl alcohol Celvol 540 solution in water, 244 g water, 1.1 g 20% NaOH, and 1.2 g DuPont Vazo-68WSP, is added to the bottom of the oil solution, using a funnel.

Mixing is again started, at 2500 rpm, for 60 minutes to emulsify the oil phase into the water solution. After milling is completed, mixing is continued with a 3" propeller at 350 rpm. The batch is held at 60° C. for 45 minutes, the temperature is increased to 75° C. in 30 minutes, held at 75° C. for 4 hours, heated to 90° C. in 30 minutes and held at 90° C. for 8 hours. The batch is then allowed to cool to room temperature. The finished microcapsules have a median particle size of 11 microns, a broadness index of 1.3, and a zeta potential of negative 0.5 millivolts, and a total scent A concentration of 19.5 wt %, and a water content of 57 wt %.

EXAMPLE 2

Spray Dried Microcapsules

To 94.85 kilograms of nonionic perfume microcapsule made by the method of example 1 is added 0.15 kilograms of Xanthan Gum powder (Novaxan Dispersible Xanthan Gum Product 174965) at a temperature of 45 degrees Centigrade, while mixing. After 25 minutes of mixing, 4.5 kilograms of a 32 wt % solution of magnesium chloride is added to the slurry (over a period of 10 minutes), then the slurry is mixed for an additional 30 minutes. Next, 1 kilogram of citric acid (anhydrous powder) is added, and mixed for 30 minutes to assure complete dissolution in the continuous phase of the slurry. This mixture is then atomized using a co-current Niro dryer, 7 ft diameter, using a rotary centrifugal wheel atomizer. The slurry is dried at an inlet air temperature of 200-220 degrees Centigrade, and outlet air temperature of 105-110 degrees Centigrade to yield a powder containing approximately 5 wt % water, a bulk density of 380 grams per Liter.

EXAMPLE 3

80 wt % Core/20 wt % Wall Urea Based Polyurea Capsule 2 grams of Urea (Sigma Aldrich of Milwaukee, Wis.) is dissolved in 20 g deionized water. 1 gram of resorcinol (Sigma Aldrich of Milwaukee, Wis.) is added to the homogeneous urea solution. 20 g of 37 wt % formaldehyde solution (Sigma Aldrich of Milwaukee, Wis.) is added to the solution, and the pH of the slurry is adjusted to 8.0 using 1M sodium hydroxide solution (Sigma Aldrich of Milwaukee, Wis.). The reactants are allowed to sit at 35° C. for 2 hours. In a separate beaker, 80 grams of fragrance oil is added slowly to the urea-formaldehyde solution. The mixture is agitated using a Janke & Kunkel Laboretechnik mixer using a pitched, 3-blade agitator to achieve a 12 micron mean oil droplet size distribution, with a standard deviation of 2 microns. The pH of the slurry is adjusted to 3.0 using 1M Hydrochloric Acid to initiate the condensation reaction. The solution is heated to 65° C. and allowed to react in a constant temperature water bath, while slowly agitating the contents of the mixture. The contents are allowed to react for 4 hours at 65° C.

EXAMPLE 4

90% Core/10 wt % Wall Melamine Based Polyurea Capsule

A first mixture is prepared by combining 208 grams of water and 5 grams of alkyl acrylate-acrylic acid copolymer (Polysciences, Inc. of Warrington, Pa., USA). This first mixture is adjusted to pH 5.0 using acetic acid.

280 grams of the capsule core material which comprise a fragrance oil is added to the first mixture at a temperature of 45° C. to form an emulsion. The ingredients to form the capsule wall material are prepared as follows: 9 grams of a corresponding capsule wall material copolymer pre-polymer (butylacrylate-acrylic acid copolymer) and 90 grams of water are combined and adjusted to pH 5.0. To this mixture is added 28 grams of a partially methylated methylol melamine resin solution ("Cymel 385", 80% solids, Cytec). This mixture is added to the above described fragrance oil-in-water emulsion with stirring at a temperature of 45 degrees Centigrade. High speed blending is used to achieve a volume-mean particle size of 12 micron, and a standard deviation of 2.6 microns. The temperature of the mixture is gradually raised to 65 degrees Centigrade, and is maintained at this temperature overnight with continuous stirring to initiate and complete encapsulation.

To form the acrylic acid-alkyl acrylate copolymer capsule wall, the alkyl group can be selected from ethyl, propyl, butyl, amyl, hexyl, cyclohexyl, 2-ethylhexyl, or other alkyl groups having from one to about sixteen carbons, preferably one to eight carbons.

EXAMPLE 5

Gelatin-gum Arabic Capsules

A gum solution is prepared by adding 1.84 grams of carboxymethyl cellulose sodium salt and 0.205 grams of gum Arabic FCC powder into 87.20 g of deionized water at a temperature of 50 degrees Centigrade, while agitating vigorously to prevent the formation of particle aggregates during powder addition. The solution is mixed until a homogeneous, transparent solution is obtained, then cooled to 35 degrees Centigrade. A gelatin solution is prepared by adding 18.45 grams of Bloom type A gelatin into 163 grams of deionized water at a temperature of 50 degrees Centigrade. The solution is cooled to 35 degrees Centigrade after the gelatin solids are completely dissolved. The gum solution is added to the gelatin solution under very low agitation (to prevent frothing/foaming). The pH of the mixture is adjusted to 5.5 using 50 wt % sodium hydroxide solution or 50 wt % citric acid solution. Approximately 180 grams of perfume oil is then added to the mixture. High agitation is pursued to achieve an volume average median droplet size of the perfume oil between 10-20 micrometers (Accusizer utilized). The solution is cooled at a rate of approximately 0.2 degrees Celsius per minute to a temperature of 28 degrees Centigrade. The pH of the solution is also slowly adjusted to 4.0 using 50 wt % citric acid. Once the polymer is observed to precipitate out of solution, the solution temperature is further lowered to 10 degrees Centigrade. Approximately 1.51 grams of 50 wt % glutaraldehyde (Sigma Aldrich) is added to the mixture, the temperature of the mixture is raided to 20 degrees Centigrade. The mixture is agitated slowly for a period of 16 hours to crosslink the shell. This aqueous suspension of gelatin microcapsules can be optionally spray dried to yield a powder.

EXAMPLES A THROUGH F

The following examples illustrated in Table 1a are formulation examples containing microcapsules. Examples A, B and C are anhydrous, antiperspirant compositions including spray-dried polyacrylate microcapsules made by interfacial polymerization, wherein the microcapsules encapsulate a fragrance and a quantity of non-volatile oils. Examples D and E are anhydrous compositions containing spray-dried polyacrylate microcapsules made by interfacial polymerization, wherein the microcapsules encapsulate a fragrance and a quantity of non-volatile oils. Example F is an anhydrous composition including spray-dried microcapsules made by a complex coacervation process that comprises reacting gelatin with an anionic colloid gum Arabic, and crosslinking with gluteraldehyde; wherein the spray-dried microcapsules encapsulate a fragrance.

Examples A and B were prepared by a batch process by adding all of the raw materials (except aluminum zirconium trichlorohydrex glycine powder, fragrance, and polyacrylate microcapsules) to a mix tank, heating the materials to a temperature of 80° C. to melt the structurants and other higher melting point ingredients, and maintaining that temperature until the ingredients are melted. Once melted, the batch is cooled to 70-75° C. and the aluminum zirconium trichlorohydrex glycine powder, fragrance, and polyacrylate microcapsules are added to the tank. The batch is then mixed for at least 15 minutes before cooling to 50-55° C. and pouring into canisters.

Example C was prepared by a split stream process. In the hot stream tank, the waxes (stearyl alcohol, castor wax, ozokerite, behenyl alcohol), emollients (C12-15 Alkyl benzoate,) and a lesser portion of the cylopentasilaxane are added into one tank, mixed, and then heated to 88° C. to melt the waxes. In the cold stream tank, the powders (actives, talc, cyclodextrins, spray-dried microcapsules), fragrances, PPG-14 butyl ether, and a greater portion of the cyclopentasiloxane are added and mixed and maintained at a temperature of less than 50° C. Once each of the hot and cold streams each is relatively homogenous, each of the process streams are simultaneously fed into a static mixer where the two streams are combined for about 5 seconds or less, ensuring a homogenous personal care composition while minimizing the mix time above the wax crystallization temperature. The personal care composition then exits the static mixer into individual canisters where the product is allowed to cool to room temperature.

Examples D, E and F are prepared in a batch process by conventional mixing techniques.

TABLE 1a

|  | Example A Polyacrylate PMC in Soft Solid made via batch process | Example B Polyacrylate PMC in Invisible Solid made via batch process | Example C Polyacrylate PMC in Invisible Solid made via Split Stream | Example D Polyacrylate PMC in cyclopentasiloxane | Example E Polyacrylate PMC in Dimethicone | Example F Gelatin PMC in Dimethicone |
|---|---|---|---|---|---|---|
| Aluminum Zirconium Trichlorohydrex Glycine Powder | 26.5 | 25.6 | — | — | — | — |
| Aluminum Zirconium Tetrachlorohydrex Gly | — | — | 25.6 | — | — | — |
| Cyclopentasiloxane | QS | QS | QS | 98 | — | — |
| Dimethicone | 5 | — | — | — | 98 | 98 |
| CO-1897 Stearyl Alcohol NF | — | 13 | 13 | — | — | — |
| Ozokerite Wax SP-1026 Type | — | 1.0 | 1.0 | — | — | — |
| Hydrogenated Castor Oil MP80 Deodorized | — | 2.90 | 2.90 | — | — | — |
| Behenyl Alcohol | — | 0.2 | 0.2 | — | — | — |
| Tribehenin | 4.5 | — | — | — | — | — |
| C 18-36 acid triglyceride | 1.125 | — | — | — | — | — |
| C12-15 Alkyl Benzoate | — | 8.5 | 8.5 | — | — | — |
| PPG-14 Butyl Ether | 0.5 | 6.5 | 6.5 | — | — | — |
| Phenyl Trimethicone | — | — | — | — | — | — |
| White Petrolatum | 3 | — | — | — | — | — |
| Mineral Oil | — | 1.0 | — | — | — | — |
| Fragrance | 0.75 | 0.75 | 0.75 | — | — | — |
| Talc Imperial 250 USP | — | 2.5 | 2.5 | — | — | — |
| Fragrance Complexed Beta-cyclodextrin | 3 | — | 3 | — | — | — |
| Polyacrylate Microcapsule | 2.0 | 2.0 | 1.5 | 2.0 | 2.0 | — |
| Gelatin Microcapsule | — | — | — | — | — | 2.0 |
| Acetyl Glucosamine | — | — | 0.01 | — | — | — |
| d-Panthenyl Triacetate | — | — | 0.01 | — | — | — |

TABLE 1a-continued

|  | Example A Polyacrylate PMC in Soft Solid made via batch process | Example B Polyacrylate PMC in Invisible Solid made via batch process | Example C Polyacrylate PMC in Invisible Solid made via Split Stream | Example D Polyacrylate PMC in cyclopentasiloxane | Example E Polyacrylate PMC in Dimethicone | Example F Gelatin PMC in Dimethicone |
|---|---|---|---|---|---|---|
| DL-ALPHA Tocopheryl Acetate (Vit E) | — | — | 0.01 | — | — | — |

QS - indicates that this material is used to bring the total to 100%.

EXAMPLES G THROUGH I

The following examples illustrated in Table 1b are formulation examples containing microcapsules and a starch encapsulated accord. Examples G, H, and I are anhydrous, antiperspirant compositions including a surfactant, Performathox 450 ethoxylate, a spray-dried polyacrylate microcapsules made by interfacial polymerization, wherein the microcapsules encapsulate a fragrance and a quantity of non-volatile oils and a starch encapsulates a fragrance as described below.

Examples G and H were prepared by a batch process by adding all of the raw materials (except aluminum zirconium trichlorohydrex glycine powder, fragrance, polyacrylate microcapsules, and starch encapsulated accord) to a mix tank, heating the materials to a temperature of 88° C. to melt the structurants, performathox 450 ethoxylate and other higher melting point ingredients, and maintaining that temperature until the ingredients are melted. Once melted, the batch is cooled to 70-75° C. and the aluminum zirconium trichlorohydrex glycine powder, fragrance, polyacrylate microcapsules and starch encapsulated accord are added to the tank. The batch is then mixed for at least 15 minutes before cooling to 50-55° C. and pouring into canisters.

Example I was prepared by a split stream process. In the hot stream tank, the waxes (stearyl alcohol, castor wax, ozokerite, behenyl alcohol), emollients (C12-15 Alkyl benzoate), performathox 450 ethoxylate and a lesser portion of the cylopentasilaxane are added into one tank, mixed, and then heated to 88° C. to melt the waxes. In the cold stream tank, the powders (actives, talc, cyclodextrins, spray-dried microcapsules, starch encapsulated accord), fragrances, PPG-14 butyl ether, and a greater portion of the cyclopentasiloxane are added and mixed and maintained at a temperature of less than 50° C. Once each of the hot and cold streams each is relatively homogenous, each of the process streams are simultaneously fed into a static mixer where the two streams are combined for about 5 seconds or less, ensuring a homogenous personal care composition while minimizing the mix time above the wax crystallization temperature. The personal care composition then exits the static mixer into individual canisters where the product is allowed to cool to room temperature.

TABLE 1b

|  | Example G Polyacrylate PMC in Soft Solid made via batch process | Example H Polyacrylate PMC in Invisible Solid made via batch process | Example I Polyacrylate PMC in Invisible Solid made via Split Stream |
|---|---|---|---|
| Aluminum Zirconium Trichlorohydrex Glycine Powder | 26.5 | 24.0 | — |
| Aluminum Zirconium Tetrachlorohydrex Gly | — | — | 25.6 |
| Cyclopentasiloxane | QS | QS | QS |
| Dimethicone | 5 | 5 | 5 |
| CO-1897 Stearyl Alcohol NF | — | 12.3 | 13.25 |
| Ozokerite Wax SP-1026 Type | — | 1.0 | 1.0 |
| Hydrogenated Castor Oil MP80 Deodorized | — | 2.75 | 2.90 |
| Behenyl Alcohol | — | 0.2 | 0.2 |
| Tribehenin | 4.5 | — | — |
| C 18-36 acid triglyceride | 1.125 | — | — |
| C12-15 Alkyl Benzoate | — | 8.5 | 8.5 |
| Performathox 450 ethoxylate | 1.0 | 1.0 | 2.0 |
| PPG-14 Butyl Ether | 0.5 | 6.5 | 6.5 |
| White Petrolatum | 3 | 3 | 3 |
| Mineral Oil | — | 8.0 | 8.0 |
| Fragrance | 0.75 | 0.75 | 0.75 |
| Talc Imperial 250 USP | — | 3 | 2.5 |
| Fragrance Complexed Beta-cyclodextrin | 2.0 | 3.0 | — |
| Polyacrylate Microcapsule | 2.0 | — | 2.0 |

TABLE 1b-continued

|  | Example G Polyacrylate PMC in Soft Solid made via batch process | Example H Polyacrylate PMC in Invisible Solid made via batch process | Example I Polyacrylate PMC in Invisible Solid made via Split Stream |
|---|---|---|---|
| Starch Encapsulated Accord | 1.0 | 0.8 | 1.5 |

QS - indicates that this material is used to bring the total to 100%.

A Starch Encapsulated Accord is made by dissolving 1025 parts of Alcocap 300 (Akzo of New Jersey, USA) in 2140 parts of water. Next, 107.9 parts of anhydrous citric acid is dissolved in the solution. 1596 parts of fragrance oil is then added, and emulsified using a high shear in-tank Arde Barinco homogenizer to yield median volume weighted average particles less than 1 microns. The slurry is then spray dried using a co-current Niro spray dryer, centrifugal wheel atomizer, operating at an inlet temperature of 200 degrees Centigrade, and outlet temperature of 95 degrees Centigrade, and a slight vacuum in the dryer. Powder is collected from the cyclone. A yield of about 85% is achieved during spray drying.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An anhydrous stick deodorant composition, comprising:
    a) one or more non-volatile liquid carriers;
    b) one or more structurants having a concentration from about 1% to about 25% by weight of the composition, wherein the one or more structurants comprises one or more waxes; and
    c) a moisture-triggered fragrance delivery system;
    wherein the stick deodorant composition is a single phase.
2. The anhydrous stick of claim 1, wherein the one or more non-volatile liquid carriers comprises a non-volatile silicone.
3. The anhydrous stick of claim 1, wherein the one or more non-volatile liquid carriers comprises a non-volatile organic fluid.
4. The anhydrous stick of claim 1, wherein the anhydrous stick composition is a soft-solid deodorant.
5. The anhydrous stick of claim 1, wherein the anhydrous stick composition is an invisible solid deodorant.
6. The anhydrous stick of claim 1, wherein the moisture-triggered fragrance delivery system comprises a starch.
7. The anhydrous stick of claim 6, wherein the starch comprises a raw starch, pregelatinized starch, modified starch, or combination thereof.
8. The anhydrous stick of claim 7, wherein the modified starch is a corn starch.
9. The anhydrous stick of claim 8, wherein the modified corn starch is an octenyl succinate.
10. The anhydrous stick of claim 9, wherein the octenyl succinate comprises a substituted waxy corn starch.
11. The anhydrous stick of claim 1, wherein the deodorant composition further comprises a volatile silicone carrier.
12. The anhydrous stick of claim 1, wherein the deodorant composition comprises from about 1% to about 20% of the non-volatile liquid carriers.
13. An anhydrous stick deodorant composition, comprising:
    a) one or more non-volatile liquid carriers;
    b) one or more structurants having a concentration from about 1% to about 25% by weight of the composition, wherein the one or more structurants comprises one or more waxes; and
    c) a friable microcapsule delivery system;
    wherein the stick deodorant composition is a single phase.
14. The anhydrous stick of claim 13, wherein the one or more non-volatile liquid carriers comprises a non-volatile silicone.
15. The anhydrous stick of claim 13, wherein the one or more non-volatile liquid carriers comprises a non-volatile organic fluid.
16. The anhydrous stick of claim 13, wherein the anhydrous stick composition is a soft-solid deodorant or an invisible solid deodorant.
17. The anhydrous stick of claim 13, wherein the friable microcapsule delivery system comprises a fragrance.
18. The anhydrous stick of claim 17, wherein the friable microcapsule delivery system comprises a starch, wherein the starch comprises a raw starch, pregelatinized starch, modified starch, or combination thereof.
19. The anhydrous stick of claim 18, wherein the modified starch is a corn starch.
20. The anhydrous stick of claim 19, wherein the corn starch is an octenyl succinate that comprises a substituted waxy corn starch.

* * * * *